US011701140B1

(12) United States Patent
Brewster

(10) Patent No.: US 11,701,140 B1
(45) Date of Patent: Jul. 18, 2023

(54) CATHETER APPARATUS FOR ARTERIAL PLAQUE REMOVAL

(71) Applicant: Parker Brewster, Oxford, MS (US)

(72) Inventor: Parker Brewster, Oxford, MS (US)

( * ) Notice: Subject to any disclaimer, the term of this patent is extended or adjusted under 35 U.S.C. 154(b) by 0 days.

(21) Appl. No.: 17/829,369

(22) Filed: Jun. 1, 2022

Related U.S. Application Data

(60) Provisional application No. 63/195,283, filed on Jun. 1, 2021.

(51) Int. Cl.
*A61B 17/3207* (2006.01)
*A61B 17/22* (2006.01)
*A61M 25/10* (2013.01)

(52) U.S. Cl.
CPC .......... *A61B 17/320725* (2013.01); *A61B 2017/22061* (2013.01); *A61M 2025/109* (2013.01); *A61M 2025/1086* (2013.01); *A61M 2025/1095* (2013.01)

(58) Field of Classification Search
CPC . A61B 17/320725; A61B 2017/22061; A61M 2025/1086; A61M 2025/109; A61M 2025/1095
See application file for complete search history.

(56) References Cited

U.S. PATENT DOCUMENTS

| | | | |
|---|---|---|---|
| 5,746,758 A | 5/1998 | Nordgren et al. | |
| 6,391,832 B2 | 5/2002 | Lyons et al. | |
| 6,893,417 B2 * | 5/2005 | Gribbons | A61M 25/09041 977/875 |
| 7,507,246 B2 | 3/2009 | McGuckin et al. | |
| 7,729,745 B2 | 6/2010 | Maschke | |
| 8,002,725 B2 | 8/2011 | Hogendijk | |
| 8,052,704 B2 | 11/2011 | Olson | |
| 8,540,758 B2 | 9/2013 | Nanavati | |
| 9,241,733 B2 | 1/2016 | Olson | |
| 10,966,749 B2 | 4/2021 | Hatta et al. | |
| 10,973,570 B2 | 4/2021 | Mathur et al. | |
| 10,980,652 B2 | 4/2021 | Sanati et al. | |
| 10,980,763 B2 | 4/2021 | Remmereit et al. | |
| 10,983,100 B2 | 4/2021 | Hazen et al. | |
| 10,987,208 B2 | 4/2021 | Schaefer et al. | |
| 10,987,452 B2 | 4/2021 | Michal et al. | |
| 10,993,737 B2 | 5/2021 | Vetter | |

(Continued)

*Primary Examiner* — Katherine M Shi
*Assistant Examiner* — Nasheha Baset
(74) *Attorney, Agent, or Firm* — Rashauna Norment

(57) ABSTRACT

An alternative to using a stent, a catheter apparatus and method removes arterial plaque within an isolated environment at a target site while separately maintaining continuous blood flow, then removed post procedure. A catheter head has a tubular array for providing a plaque treatment solution within a first layer of the catheter apparatus without the same entering the blood stream, and for receiving a guide-wire to position the apparatus at the target site. The first layer has a plurality of flap members, with each defining an air pressure regulated pore for plaque removal using an inflow tube and an outflow tube. A separate second layer of the catheter apparatus accommodates continuous blood flow during the procedure. A third layer of the catheter apparatus contains the selectively inflatable balloon. When the balloon is inflated, the catheter head and the catheter end cap each inflate to supports the arterial wall.

16 Claims, 15 Drawing Sheets

(56) References Cited

U.S. PATENT DOCUMENTS

| | | |
|---|---|---|
| 10,993,824 B2 | 5/2021 | Longo |
| 11,000,185 B2 | 5/2021 | Stigall et al. |
| 11,000,304 B2 | 5/2021 | Tada et al. |
| 11,000,393 B2 | 5/2021 | Bourang |
| 11,007,075 B2 | 5/2021 | Bagaoisan et al. |
| 11,017,534 B2 | 5/2021 | Hsieh et al. |

\* cited by examiner

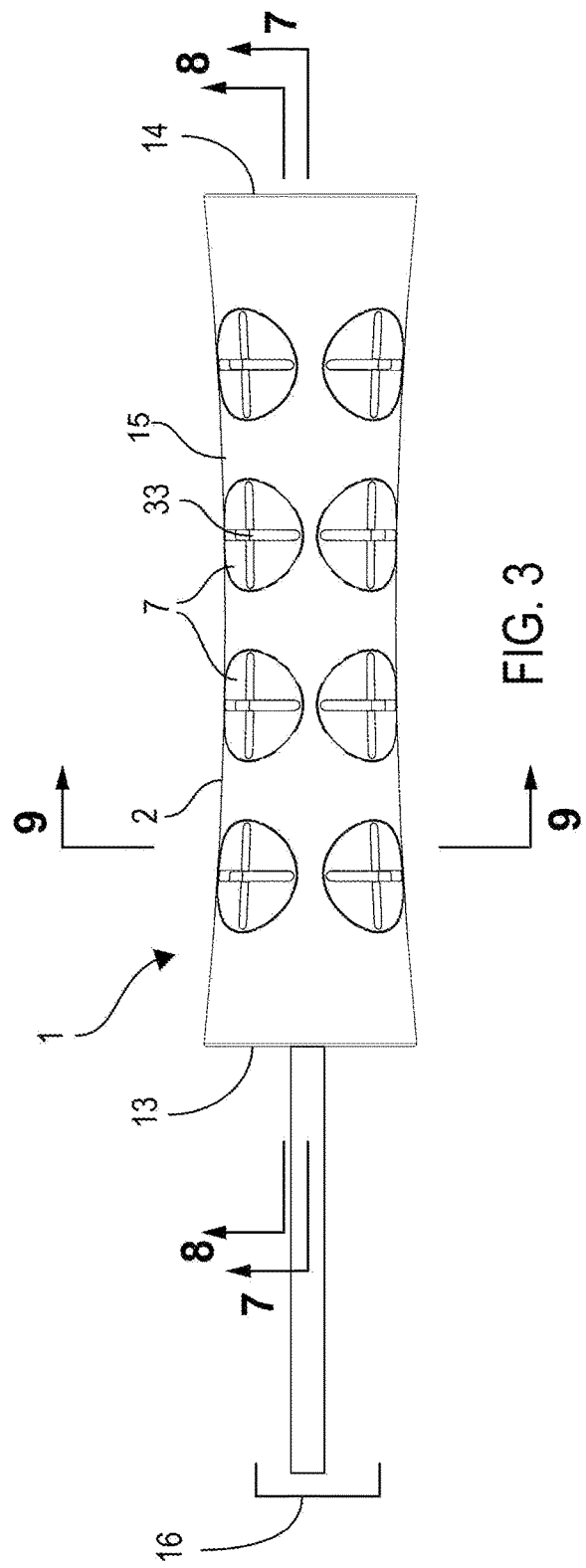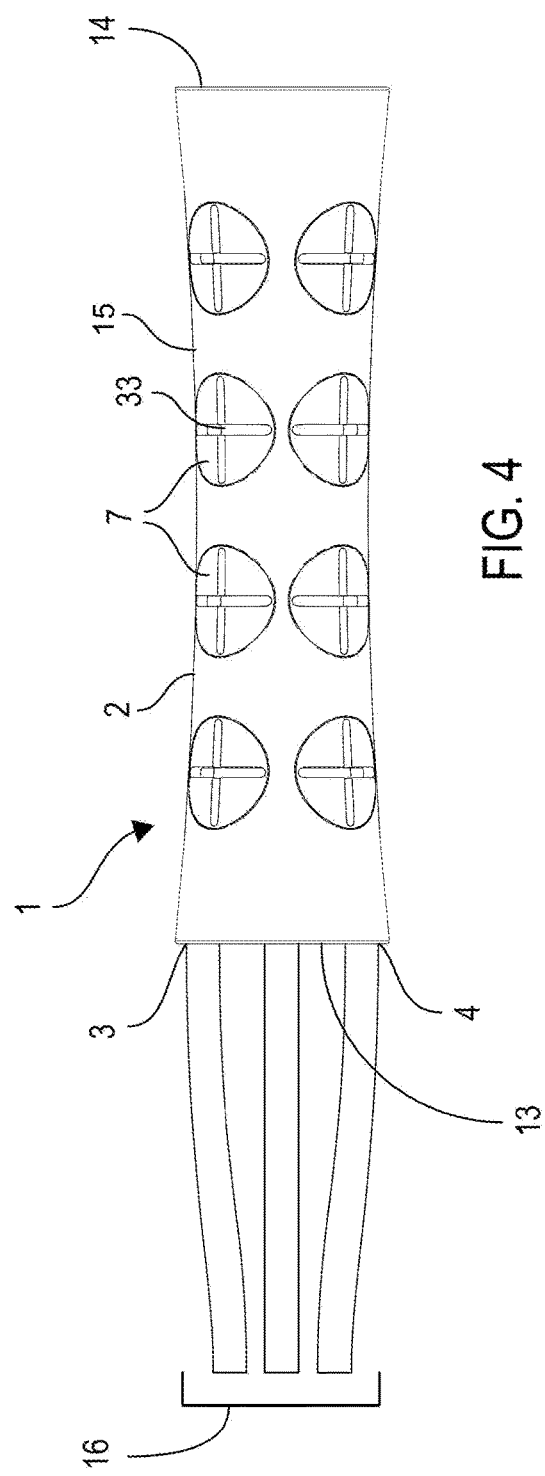

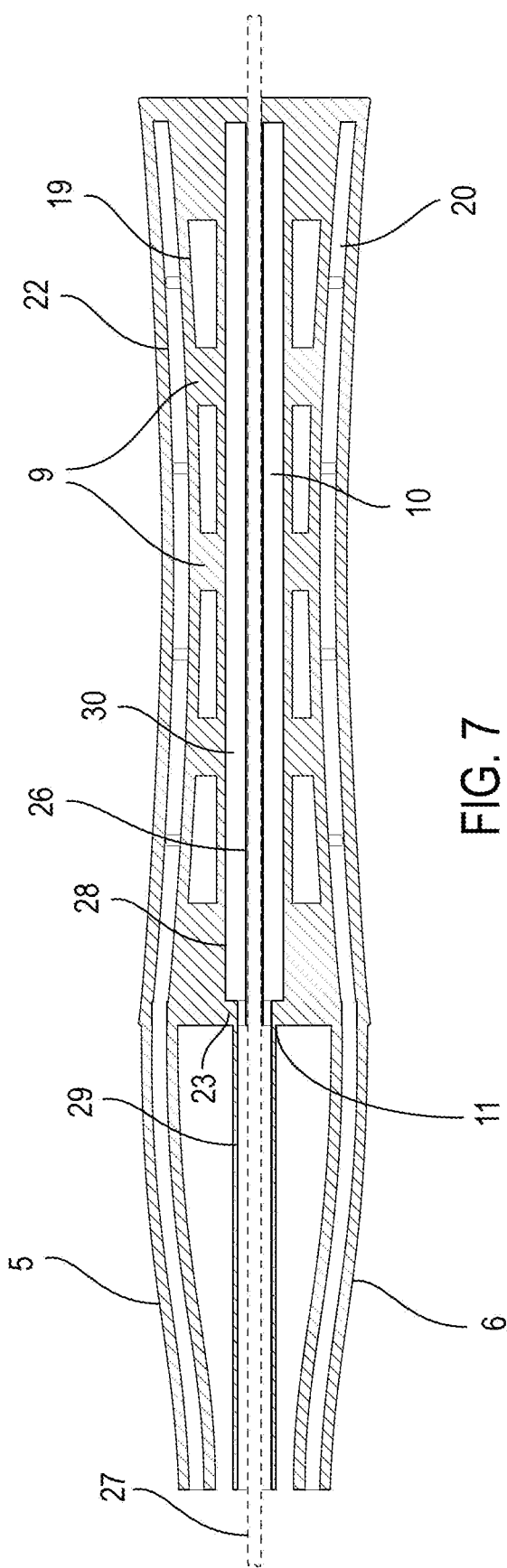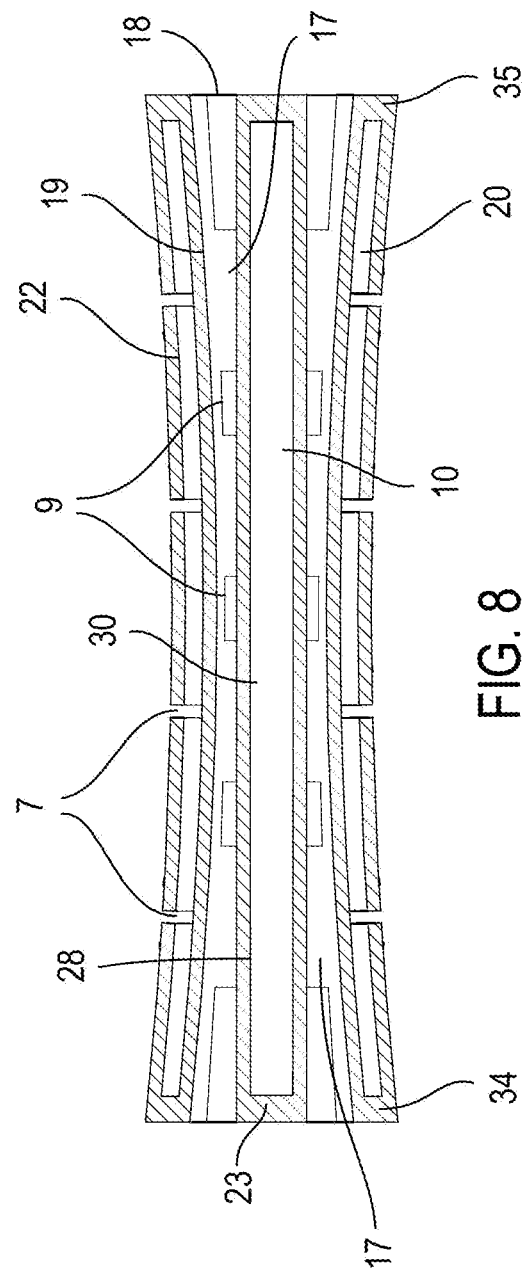
FIG. 7
FIG. 8

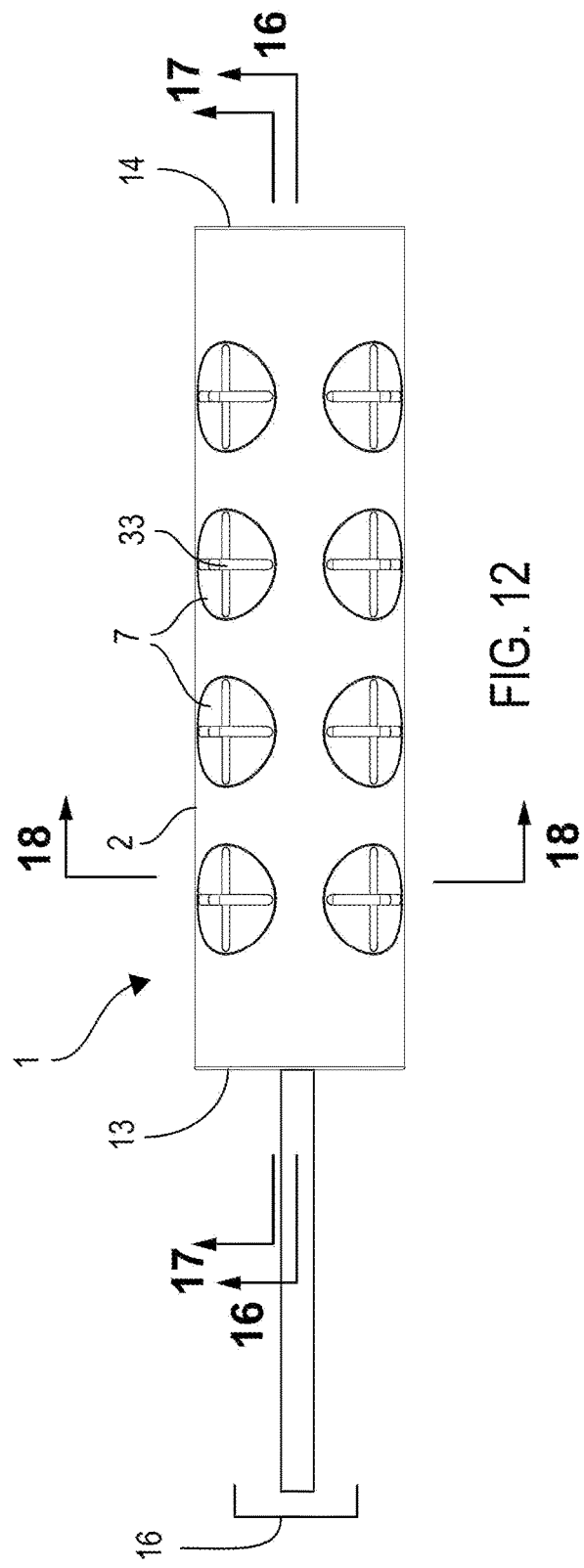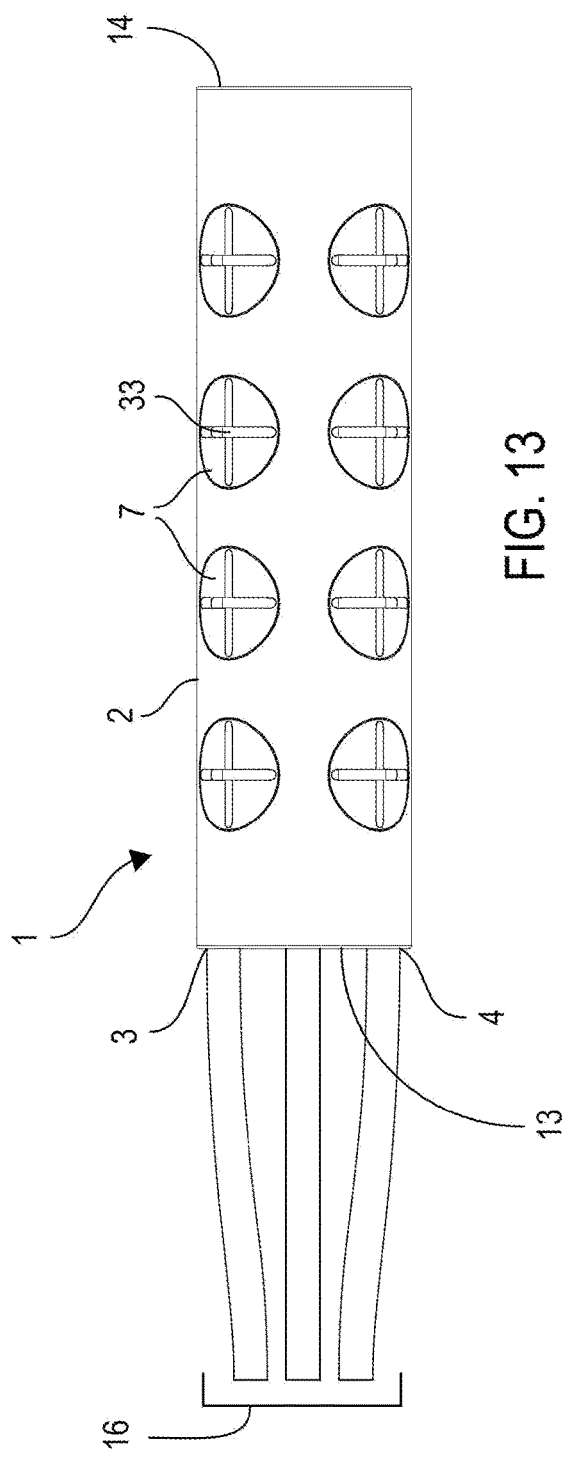

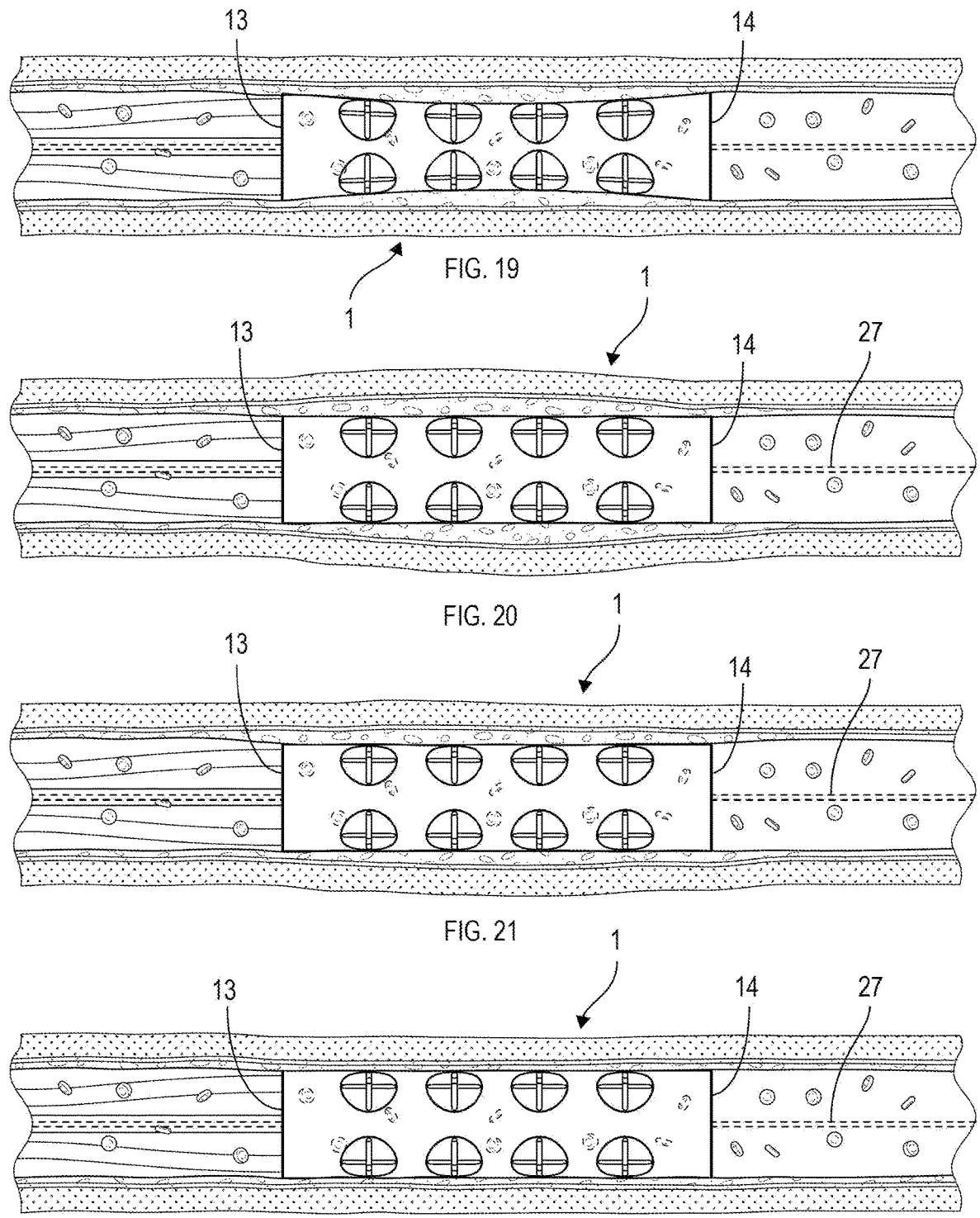

CATHETER APPARATUS FOR ARTERIAL PLAQUE REMOVAL

CROSS-REFERENCE TO RELATED APPLICATIONS

This application claims the benefit of and priority of U.S. Provisional Patent Application No. 63/195,283, filed on Jun. 1, 2021, which is incorporated herein by reference.

FEDERALLY SPONSORED RESEARCH AND DEVELOPMENT

Not applicable.

BACKGROUND OF THE INVENTION

1. Field of the Invention

The present invention generally relates to a catheter apparatus for arterial plaque removal during a treatment procedure, with the apparatus having a selectively inflatable balloon catheter to create an isolated environment at the target site, to facilitate removal of arterial plaque without stenting, and to maintain continuous blood flow during the treatment procedure.

2. Description of Arguably Related Art Including Information Disclosed for 37 CFR 1.97 and 1.98

Stenosis or plaque arterial blockage or hard deposit buildup (collectively, "plaque") along the walls of the blood vessels can partially block blood flow. Such blockage often requires surgical intervention for plaque removal. Various treatments and devices have been previously used for plaque removal; however, current plaque removal treatments are often too dangerous when used to remove plaque in peripheral arteries, namely, with patients diagnosed with peripheral artery disease (PAD) and coronary artery disease (CAD). The particular procedure and selected treatment for plaque removal generally depend upon the amount of plaque blockage in the impacted artery, and upon the size and location of the impacted artery.

Some conventional procedures and associated devices are currently utilized for arterial plaque removal. Some of these procedures include, but are not limited to, angioplasty with stenting, endarterectomy, and atherectomy. In general, these procedures concern either inflating the blocked arterial wall for plaque compression against the arterial wall, or alternatively, grinding, shaving, or directly cutting plaque away from within the artery. Each procedure poses various potential risks and complications either during the procedure itself or in post-procedure. Complications can arise after these procedures including increased risks for infection.

With an angioplasty procedure, a balloon-tipped catheter is directed to the site of the arterial plaque, then the balloon is inflated to expand the arterial wall and to compress the arterial plaque against the arterial wall. A stent is generally employed with the balloon-tipped catheter either during or immediately after plaque removal. Some stents are metal or composite lattice tube that are meant to hold or to further expand the freshly widened artery. The stent may also cover the compressed plaque. New tissue will grow into the stent so that the stent becomes part of the lining of the artery. Modern stents are often medicinally coated in an attempt to prevent the artery from closing post-procedure. An angioplasty procedure also uses a sheath and a guide-wire. The sheath is essentially a vascular tube placed into the access artery, for example, the femoral artery or the radial artery. The guide-wire is essentially a thin wire used in the placement of the catheter. Two different methods are available for delivering the air to inflate the balloon. An older, more common method requires delivering a pre-set amount of air to inflate the balloon at the site of the arterial plaque. A newer method uses sensors within the catheter to deliver a patient-specific amount of air pressure or volume to inflate the balloon at the site of the arterial plaque.

Some complications and limitations with using a stent during an angioplasty procedure include, but are not limited to, local and dispersed infections due to leaving a foreign body (the stent) inside the artery post-procedure, requirements of additional points of attachment of the stent to the artery (accumulation), stent dislodgment or stent failure, restenosis inside the stent, and early and late stent thrombosis requiring anti-platelet drugs and therapies. Other problems include, but are not limited to, difficulty to stent lesions lying at or near bifurcation points, and the inability to use a stent for arteries having significant plaque buildup or use with smaller arteries. Using stents often create conditions that require rehospitalization after rehospitalization. Furthermore, coronary stent infections are the most lethal of any hospital-acquired infection. Angioplasty with stenting is further limited for smaller arteries. The effectiveness of using stents with angioplasty is under critical review by the medical community.

With a general atherectomy procedure, one procedure provides cutting away and removing the plaque using a rotating blade rather than compressing the plaque into the artery wall. Examples of atherectomy procedures are rotablation (rotational atherectomy), directional coronary atherectomy, and extraction atherectomy. With a rotablation procedure, a catheter having an acorn-shaped, diamond-coated tip is guided to the location where the coronary artery narrows over a narrow guide-wire that extends from the device. The catheter tip is actuated and spins at a high speed to grind away the plaque from the impacted artery walls. The arterial wall is pushed away from the drill head and is not generally damaged during the procedure. See U.S. Pat. No. 7,729,745 issued to Maschke, column 1. The removed plaque particles or residuals are typically small enough to pass through the blood stream without further blocking narrow vascular channels. See U.S. Pat. No. 6,391,832 issued to Lyons, et al., column 1.

With an endarterectomy procedure, an incision is made directly in the patient's neck and to the affected artery, then the arterial plaque is directly removed from that incision. A temporary flexible tube is often inserted into the artery to maintain blood flow as the plaque is cleared. After plaque removal, the artery and neck incisions are closed with stitches. An endarterectomy is almost exclusively used in the carotid artery, which is commonly referred to as carotid artery surgery. However, this procedure is dangerous and not performed in tighter places in the arteries.

The most important signifier showing the lack of quality is the countless studies showing that current interventional methods are not proving to be more effective than modern medications: statins, beta blockers, nitrates, and ACE inhibitors. Reconsideration of these interventional methods is critical. Some practitioners have limited using the above mentioned procedures and a need remains for a more efficacious means.

Problems with stenting and angioplasty include, but are not limited to, restenosis; additional points of attachment (accumulation); leaving a foreign body in the artery which may lead to both local infection and dispersed infection; less effective than when using safer and cheaper statins; marked difficulty to stent lesions lying at or near bifurcation points in the artery; procedure requiring higher pressure which permanently disfigures arterial tissue; early stent thrombosis requiring anti-platelet drugs; and catastrophic events including late stent thrombosis often from using coated stents. Coated stents help prevent restenosis, but increase chances of late stent thrombosis. Use of a stent during arterial plaque removal requires long-term medical therapy.

With these angioplasty with stenting procedures, continuing anti-platelet therapies for at least six months are recommended. A risk with continued anti-platelet therapies is that the patient becomes more prone to bleeding problems. When a patient is more prone to bleeding problems, minor accidents and injuries unrelated to the procedure can lead to fatal bleeding. Stopping DAPT, even several years after the angioplasty procedure, may cause an immediate spike in the stent thrombosis incident.

Angioplasty with stenting is not the only procedure available in every arterial plaque blockage scenario. For example, if a patient has significant blockage while not producing any symptoms, angioplasty with stenting may not be the best treatment option. Medical therapy and lifestyle changes may have a better post-treatment outcome than the angioplasty procedure. Angioplasty with stenting has been previously used for stable angina, but the effectiveness of such procedure may not outweigh the above listed risks.

Problems with endarterectomy include, but are not limited to, invasive and visible neck scarring post-procedure; bleeding at the incision site at the neck; blocked airway from swelling or from bleeding in the neck; stroke or TIA; heart attack; blood pooling into the tissue around the incision site which causes swelling; nerve problems with certain functions of the eyes, nose, tongue, or ears; intracerebral hemorrhage; seizures (albeit uncommon); repeated blockage of the carotid artery; new blockage that develops on the artery on the opposite side of the patient's neck; infection; high blood pressure; and irregular heartbeat. As with these angioplasty with stenting procedures, continuing anti-platelet therapies for at least six months after an endarterectomy is recommended. The risk of bleeding problems and complications are the same. Also, stopping DAPT, even several years after the endarterectomy procedure, may cause an immediate spike in the stent thrombosis incident.

Problems with general atherectomy include, but are not limited to, long-term adverse outcomes. Five-year amputation rate is more likely to occur after this procedure than after a stenting procedure with similar predetermined plaque ratings.

A need exists for an apparatus and arterial plaque removal procedure that removes plaque from at least peripheral arteries and that leaves no foreign bodies behind in the patient's body, for example, a stent, post treatment.

A need exists for an apparatus and arterial plaque removal procedure that allows continuous, uninterrupted blood flow during plaque removal.

A need exists for an apparatus and arterial plaque removal procedure that creates an isolated environment during the plaque removal treatment that isolates and removes plaque without the plaque entering the blood stream while simultaneously maintaining continuous blood flow during the treatment procedure.

None of the patent references disclose the invention.

SUMMARY OF THE INVENTION

Due to the described disadvantages inherent in the known types of balloon catheters and arterial plaque removal devices, the present invention provides a new and improved apparatus and method for arterial plaque removal during a treatment procedure using a selectively inflatable balloon catheter without stenting that provides continuous blood flow during plaque removal while creating an isolated environment of the target site to remove plaque without the plaque or a treatment solution from entering the blood stream. It is understood that the present invention is not limited in its application to the details of construction or to the arrangement of the components described in the following illustrated drawing or in the detailed description.

In general, the invention discloses an improved catheter having a proximal end (or proximal head, or catheter head), a longitudinal body, and a distal end (or catheter end cap). The catheter body comprises three distinct layers or regions: a first, outermost layer or an outer sleeve; a second, middle layer or a hollow chamber, and a third, innermost layer or a core sheath. A selectively inflatable balloon, and consequently the catheter, is biased in a deflated configuration. The balloon is tighter or narrower in the middle of the balloon during balloon inflation. The balloon is more elastic at each opposing end portion of the balloon for expansion or stretching during balloon inflation. The inflated and expanded structure of the opposing end portions of the catheter creates an isolated environment at the target site for plaque removal.

The hollow chamber has a plurality of strut members spaced apart therein and configured to maintain blood flow while the balloon, the catheter head, and the catheter end cap are inflated and while plaque is being removed from the target site. The outermost, first layer of the apparatus provides for solution input and solution output through the respective sleeve tubes, or respective inflow tube and outflow tube.

At the beginning of the treatment procedure, the catheter apparatus is positioned at the target site. Here, the catheter apparatus and the balloon within the third layer of the catheter apparatus are in a biased, deflated configuration. During the treatment procedure, the balloon is actuated and inflated using an inflating mechanism, wherein the opposing end portions of the balloon expands and inflates. The expanding balloon causes the catheter head and the catheter end cap to also expand, resulting in the catheter head and the catheter end cap each abutting against the arterial wall and creating an isolated environment for direct access to the plaque for treatment. Continuous blood flow is maintained through the plurality of openings defined along the length of the chamber or second layer of the catheter body. Once the artery wall is stabilized, the plaque dissolvent solution is supplied through the inflow tube, or first sleeve tube of the tubular array, and removed through the outflow tube, or second sleeve tube of the tubular array. The plaque dissolvent solution may also be referred to in this disclosure as "plaque solvent" or part of the "treatment solution."

The distal portion of the first sleeve tube extends within the outer sleeve of the catheter body. Pressure from the plaque solvent is expelled from the inflow, first sleeve tube through the at least one pore of the plurality of flap members to the target site to break down, dissolve, or otherwise react with the targeted arterial plaque. During the inflow process, the structural design of the plurality of flap members and the corresponding pores allow the plaque solvent to reach the plaque while minimizing blood flow leakage within the isolated environment. Because the catheter apparatus includes separate, independent layers, the treated plaque does not leave the outer sleeve or first layer treatment area except through the outflow, retrieval, second sleeve tube.

The removed plaque remains isolated and does not freely flow within the chamber to commingle with the blood that continuously flows through the catheter openings.

After providing the plaque solvent, an external pressure or vacuum is applied to the outflow tube to essentially vacuum out or otherwise remove the plaque from the target site. The applied vacuum pressure essentially pulls the plaque and associated debris back through the pores of the flap members into a distal open end of the outflow tube and out the patient's body for disposal. The plaque treatment and removal steps may be repeated as necessary. Depending on the amount of plaque to be removed, the catheter apparatus may also need to be adjusted at the target site.

Due to the structure of the apparatus when inflated, it is useful to isolate the plaque at the target site, but also to utilize the apparatus as a temporary, structural stent or arterial wall support so that the procedure may be completed or repeated while maintaining continuous blood flow. A separate inflow tube from the outflow tube is preferred. After plaque removal is completed, the vacuum or pressure imparted through the outflow, second sleeve tube is disengaged and the balloon inflating mechanism is deactivated. The balloon returns to a biased, deflated configuration, which in turn, releases the tension applied to the catheter head and the catheter end cap. The catheter head, the catheter body, and the catheter end cap return to the biased, deflated substantially cylindrical configuration. Lastly, the entire catheter apparatus is withdrawn from the target site and slidably travels along the guide-wire to a different target site or to be removed from the patient's body.

The apparatus is a safer alternative treatment option to using a stent because use of this apparatus does not leave foreign bodies within the artery. The apparatus does not restrict blood flow and does not impair the arterial wall. This procedure will improve patient recovery and post-treatment outcome related to the procedure.

It is an object of this invention to provide an apparatus and arterial plaque removal procedure that removes plaque from at least peripheral arteries and that leaves no foreign bodies behind in the body, for example, a stent.

It is an object of this invention to provide an apparatus and arterial plaque removal procedure that allows continuous, uninterrupted blood flow during the plaque removal treatment procedure.

It is another object of this invention to provide an apparatus and arterial plaque removal procedure that creates an isolated environment during the plaque removal treatment that isolates and removes plaque without the plaque entering the blood stream while simultaneously maintaining continuous blood flow during the treatment procedure.

These and other aspects, objects, embodiments, and advantages of the invention will become apparent from the accompanying drawing and the following detailed description of the preferred embodiments of the invention.

BRIEF DESCRIPTION OF THE SEVERAL VIEWS OF THE DRAWING

The invention may be more readily described by reference to the accompanying drawing figures and the following description of the drawing figures. The reference numbers apply to each embodiment of the invention. In the drawing:

FIG. 3 a first side elevation view of FIG. 1, with the opposing second side elevation view being a mirror image thereof;

FIG. 4 is a third side elevation view of FIG. 1, with the opposing fourth side elevation view being a mirror image thereof;

FIG. 7 is a lateral cross-section view of FIG. 3, showing the balloon deflated before the catheter head and the catheter end cap have each deflated or retracted;

FIG. 8 is another lateral cross-section view of FIG. 3, showing the balloon deflated before the catheter head and the catheter end cap have each deflated or retracted;

FIG. 12 a first side elevation view of FIG. 10, with the opposing second side elevation view being a mirror image thereof;

FIG. 13 is a third side elevation view of FIG. 10, with the opposing fourth side elevation view being a mirror image thereof;

FIG. 19 is a side elevation view of FIG. 1, showing the catheter apparatus in a deflated configuration, shown in use at a target site within an artery having plaque and showing unobstructed blood flow;

FIG. 20 is a side elevation view of FIG. 10, showing the catheter apparatus in an inflated configuration, shown in use at a target site within an artery having plaque and showing unobstructed blood flow;

FIG. 21 is another side elevation view of FIG. 20, showing plaque nearly gone from the artery;

FIG. 22 is another side elevation view of FIG. 20, showing no plaque in the artery after plaque removal treatment;

Figure 1:
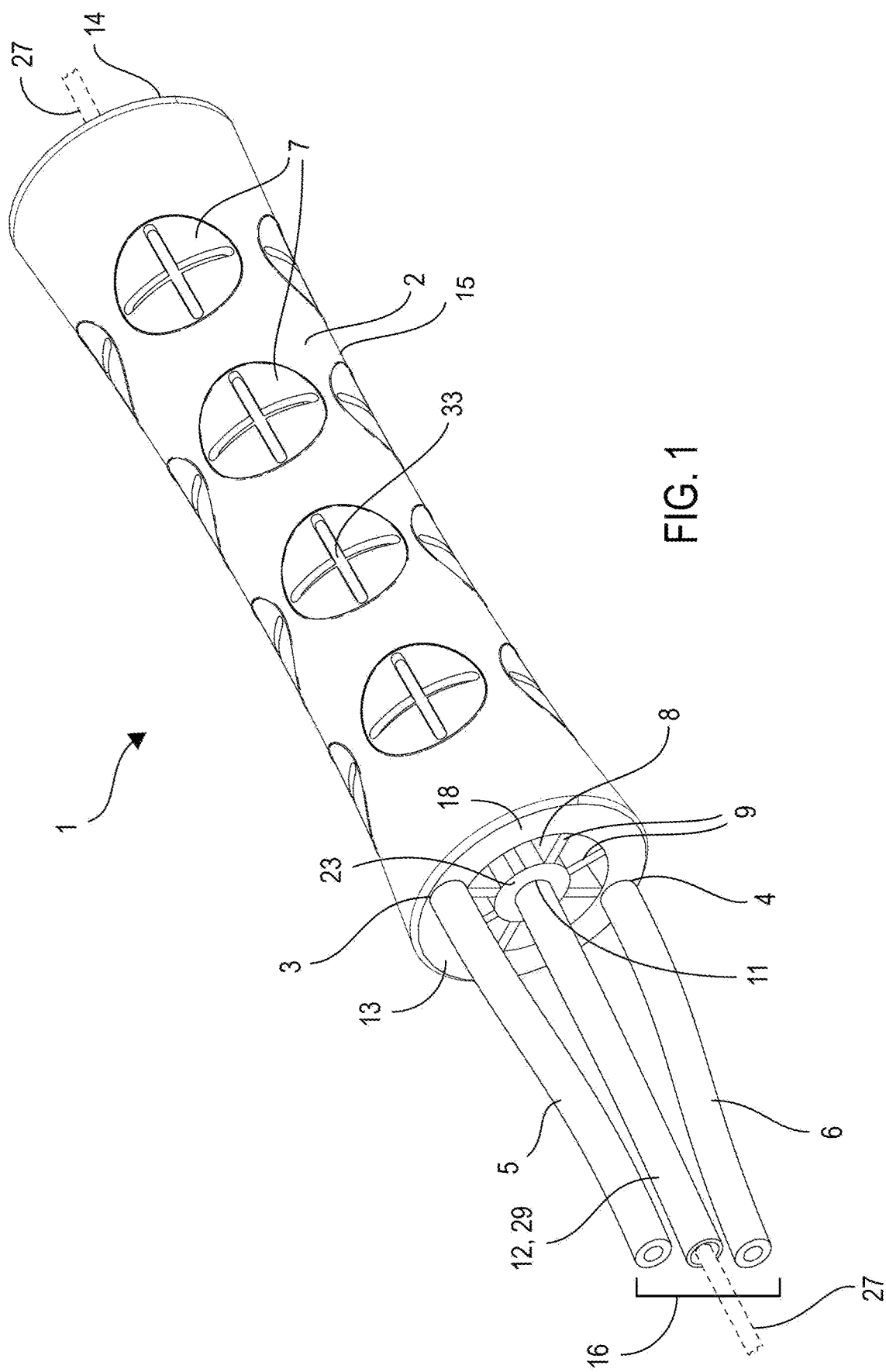
FIG. 1 is a perspective view of the catheter apparatus, showing the catheter apparatus in an inflated configuration, with the catheter head and catheter end cap shown in a flared, inflated, or expanded configuration in relation to the catheter body.
Figure 2:
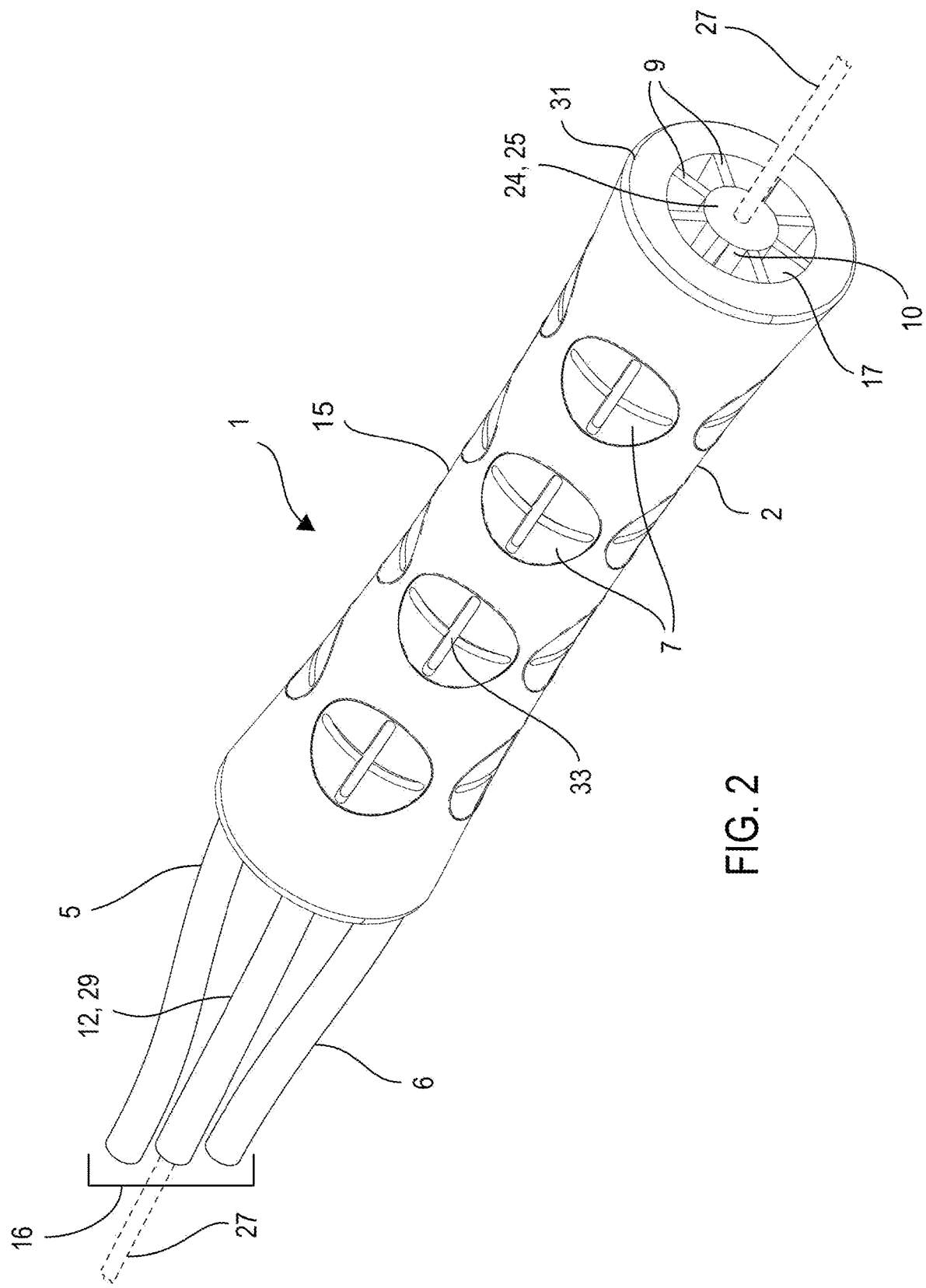
FIG. 2 is a rear perspective view of FIG. 1.
Figure 6:
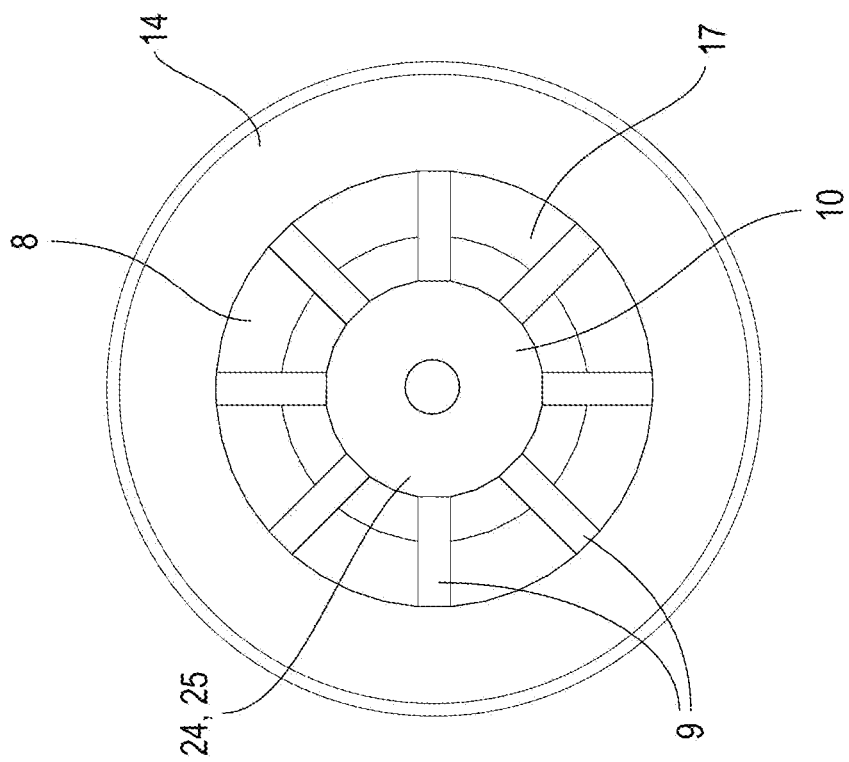
FIG. 6 a bottom plan view of FIG. 1.
Figure 5:
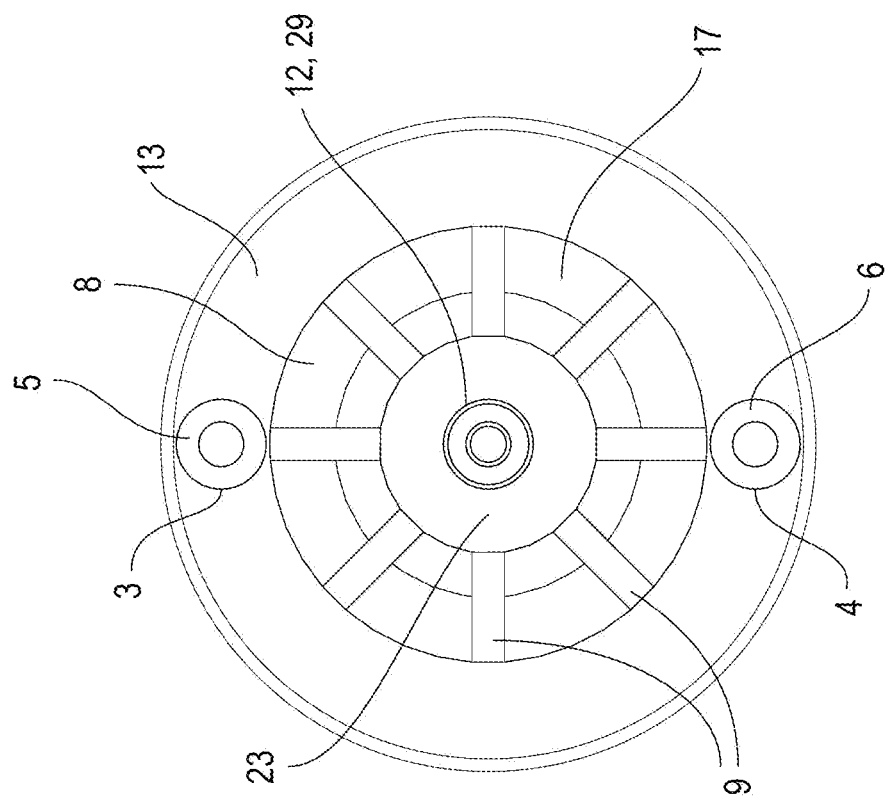
FIG. 5 is a top plan view of FIG. 1.
Figure 9:
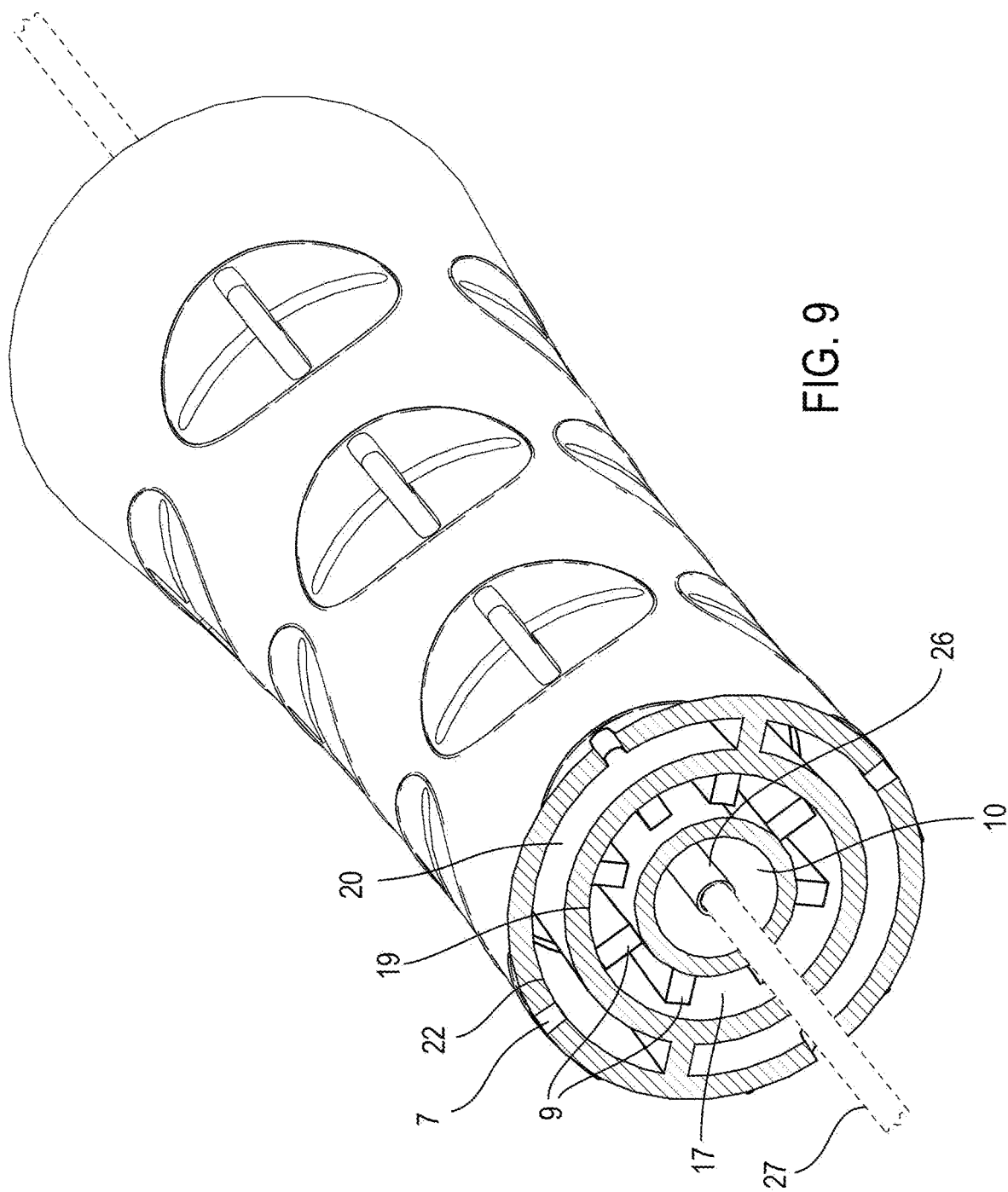
FIG. 9 is a terminal end cross-section of FIG. 3.
Figure 10:
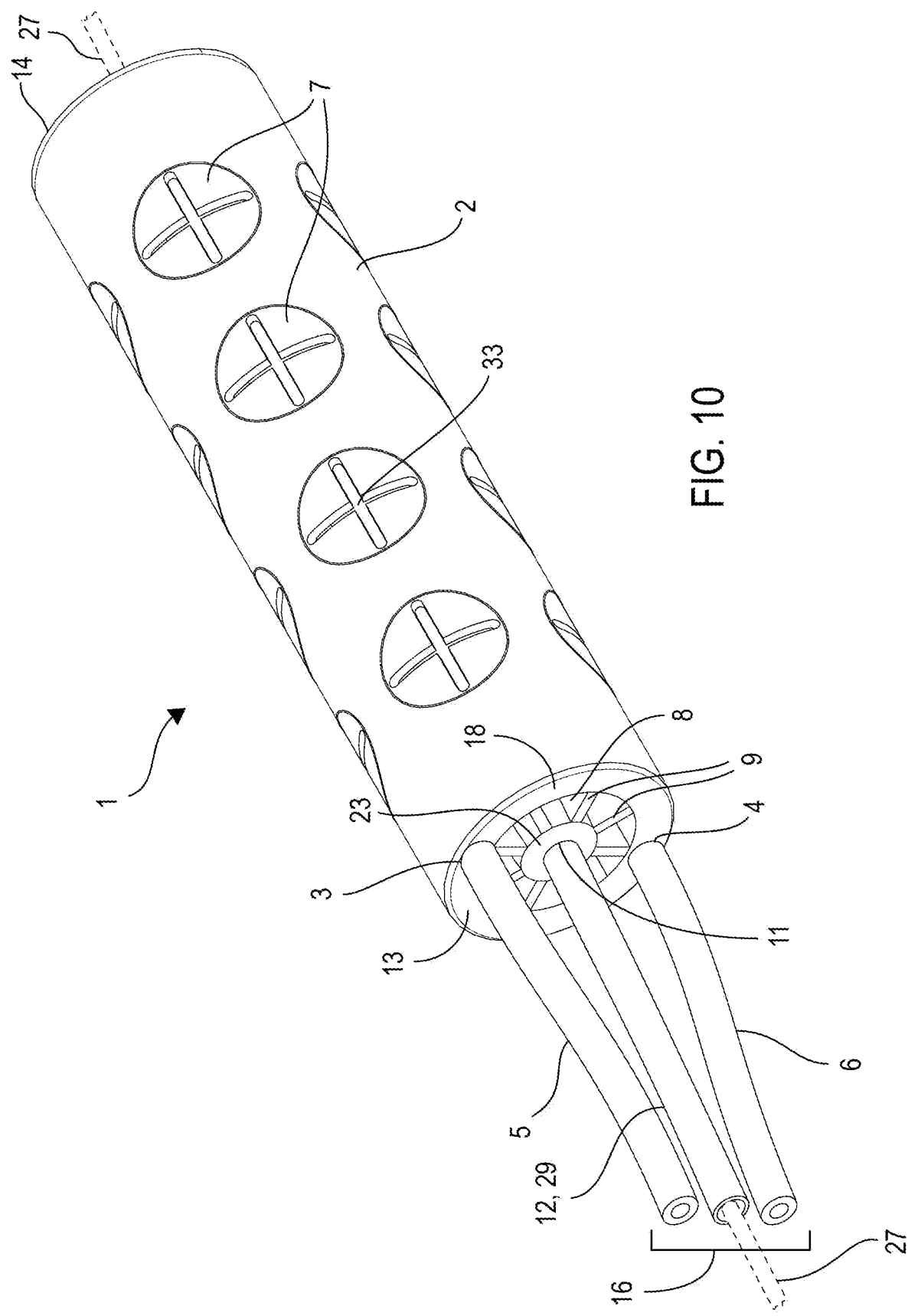
FIG. 10 is a perspective view of FIG. 1, showing the catheter apparatus in a biased, deflated configuration, with the catheter head, catheter end cap, and catheter body forming a substantially cylindrical catheter member.
Figure 11:
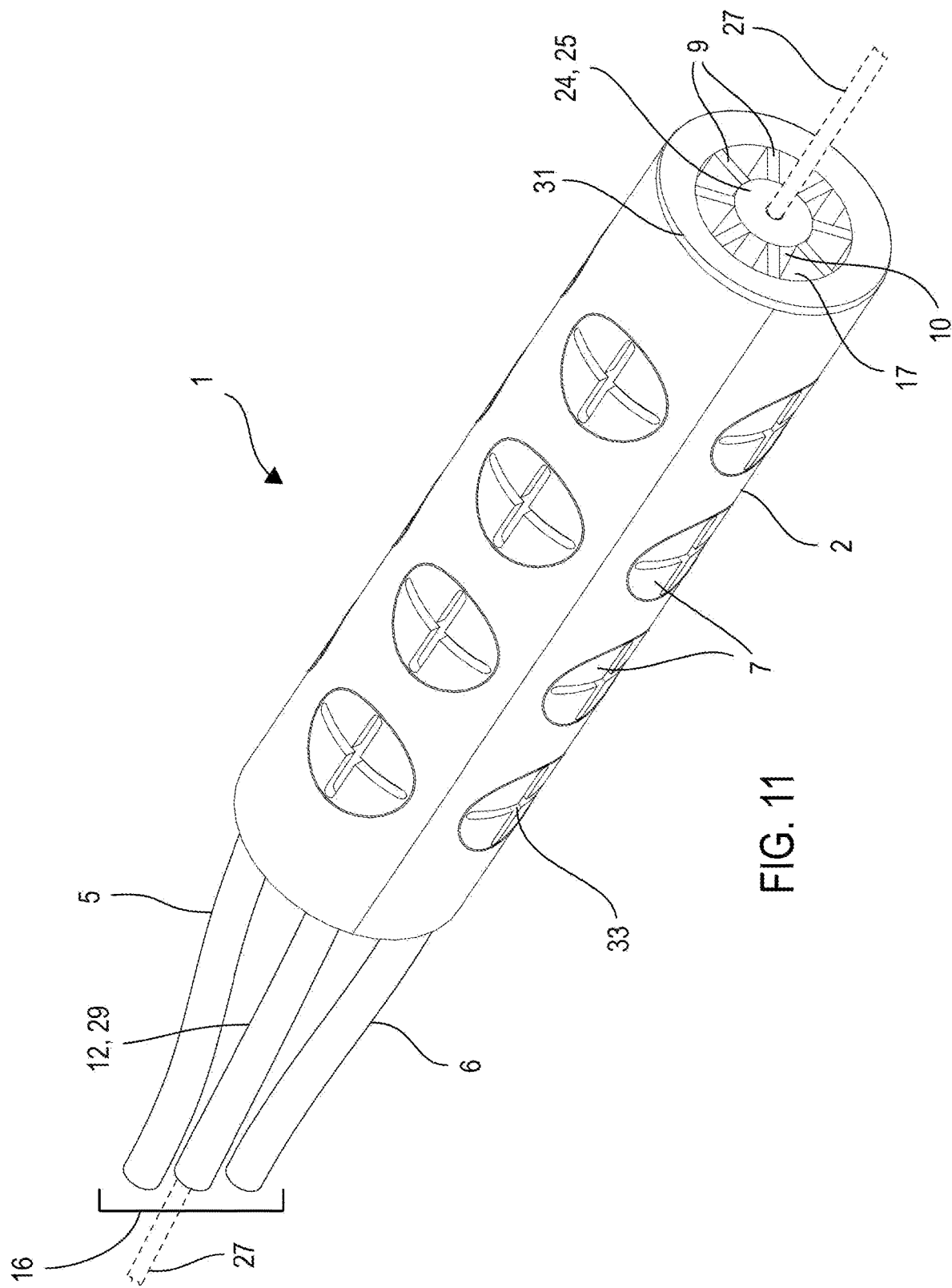
FIG. 11 is a rear perspective view of FIG. 10.
Figure 15:
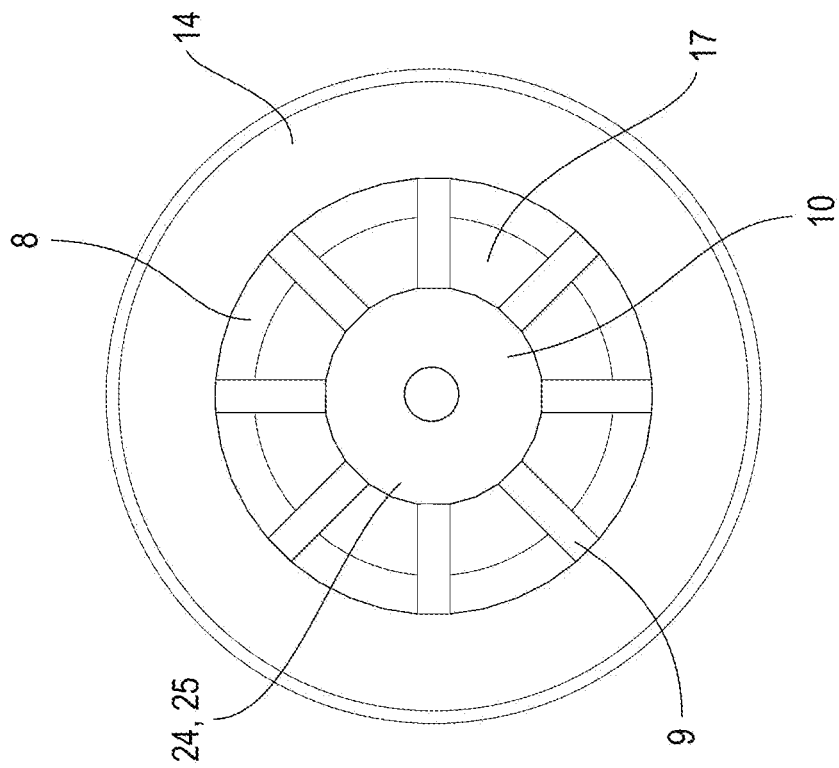
FIG. 15 a bottom plan view of FIG. 10.
Figure 14:
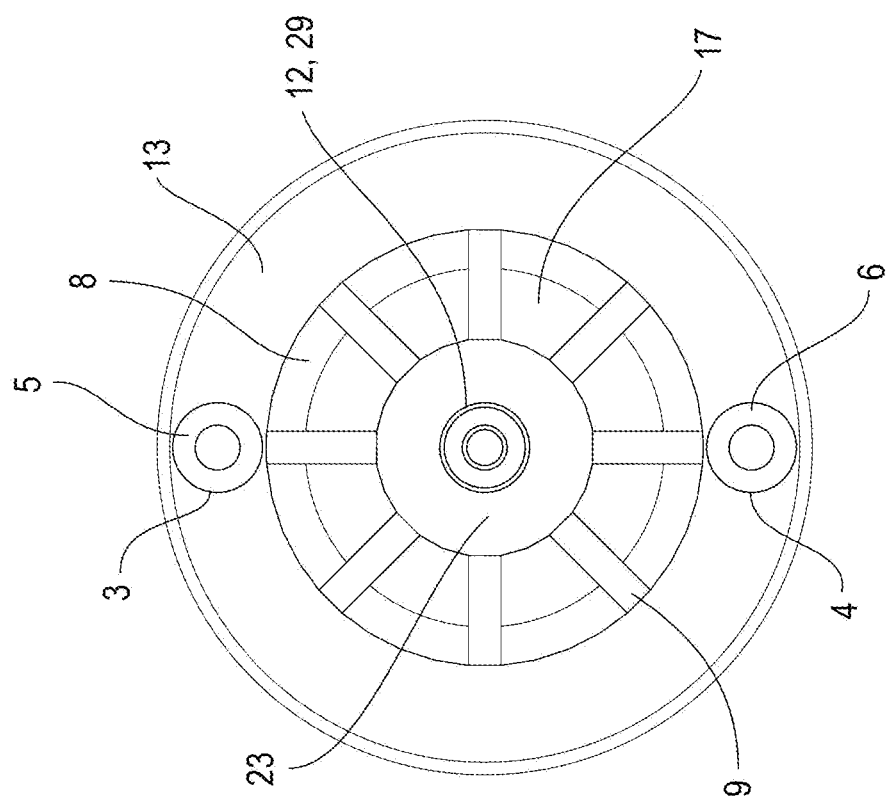
FIG. 14 is a top plan view of FIG. 10.
Figure 16:
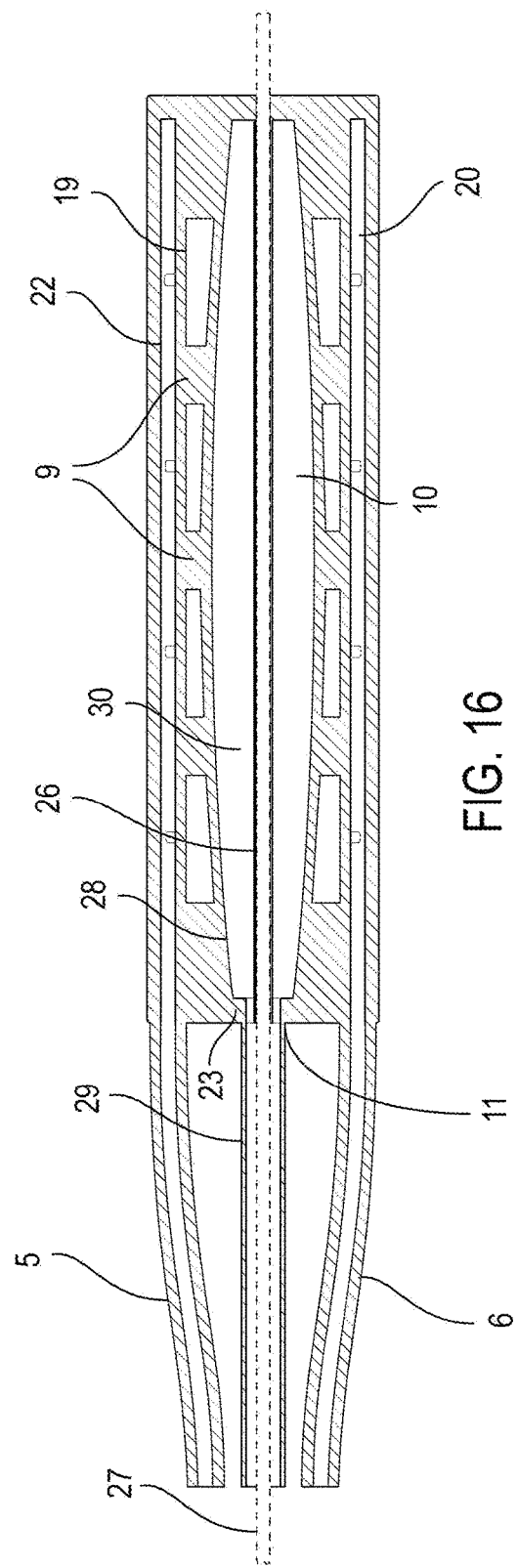
FIG. 16 is a lateral cross-section view of FIG. 12, showing the balloon inflated before the catheter head and the catheter end cap have each inflated or expanded.
Figure 17:
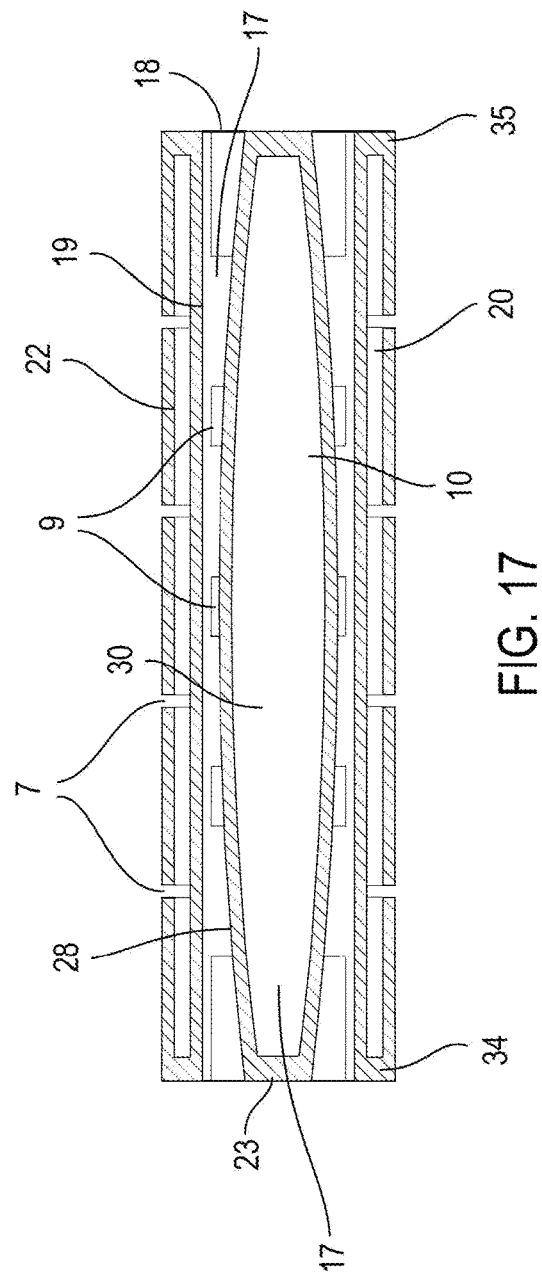
FIG. 17 is another lateral cross-section view of FIG. 12, showing the balloon inflated before the catheter head and the catheter end cap have each inflated or expanded.
Figure 18:
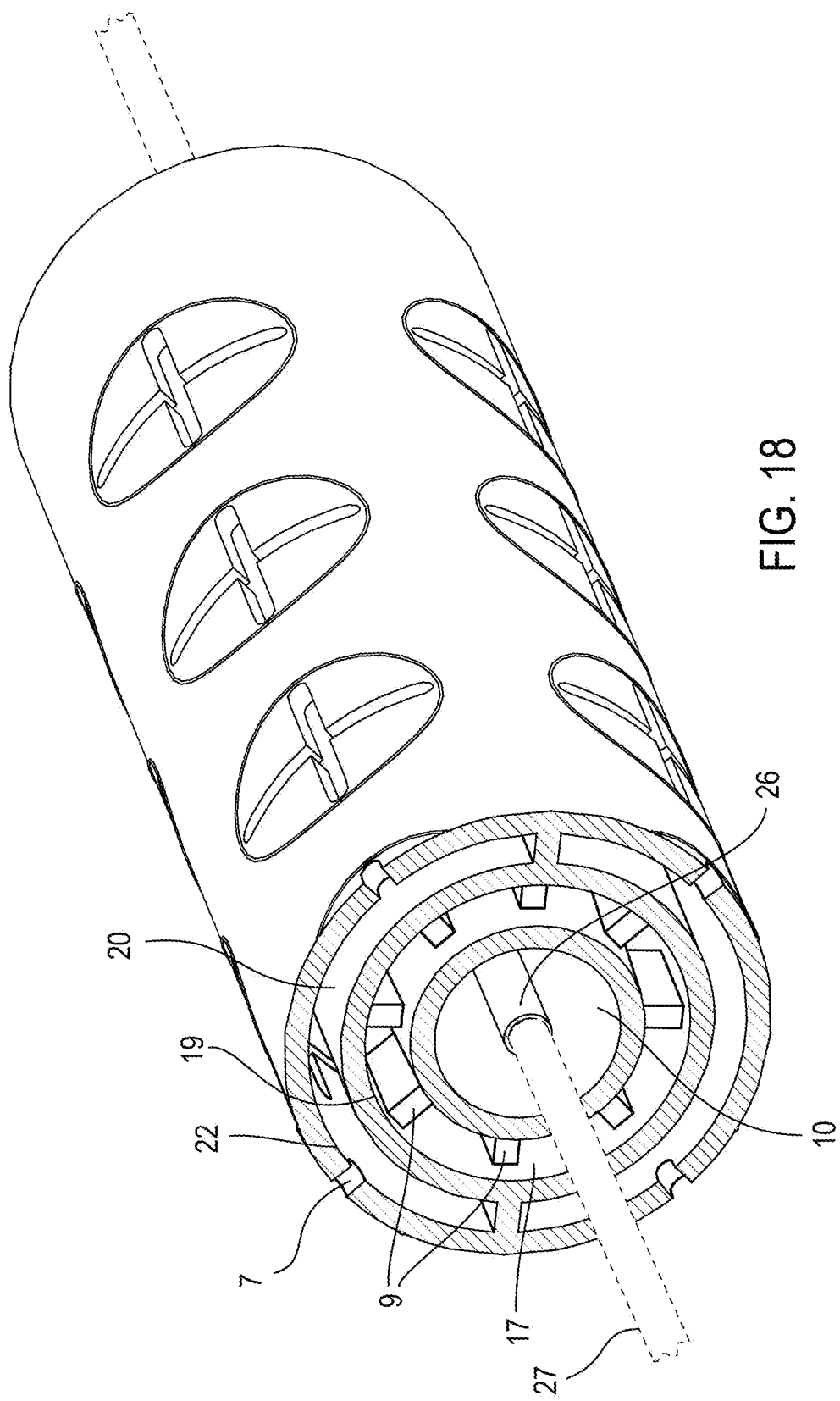
FIG. 18 is a terminal end cross-section of FIG. 12.

The broken lines represent a guide-wire, blood cells, plaque, and arterial wall are for illustrative purposes only.

DETAILED DESCRIPTION OF THE INVENTION

The present invention, preferred embodiments of the invention, and the accompanying drawing figures as described herein should not be construed as limited to the illustrated drawing. Rather the illustrated embodiment(s) are detailed to provide a thorough disclosure suitable to convey the scope of the invention to those skilled in the art. For the sake of simplicity, the conjunctive "and" may also be taken to include the disjunctive "or," and vice versa, whenever necessary to give the claims of this patent application the broadest interpretation and construction possible. Likewise, when the plural form is used, it may be taken to include the singular form, and vice versa.

Referring more particularly to the drawing by characters of reference, FIGS. 1-26 depict an improved catheter apparatus, with the components shown in a deflated configuration, an inflated configuration, and in use with environment. In general, the invention is an improved catheter apparatus for arterial plaque removal during an angioplasty procedure that creates an isolated environment for plaque removal at a target site while maintaining continuous blood flow during the treatment procedure.

In a preferred embodiment, the invention is a catheter apparatus 1 for arterial plaque removal in an isolated environment while maintaining continuous blood flow in a bloodstream during a treatment procedure, with the catheter apparatus 1 being insertable over a guide-wire and positioned at a target site during the treatment procedure, the catheter apparatus comprising (including or having):

a. a catheter head 13 at a proximal end of the catheter apparatus 1;
b. a catheter body 15;
c. a catheter end cap 14 at a distal end 14 of the catheter apparatus 1; and
d. a balloon 30 within the catheter body 15, with the balloon 30 being biased in a deflated configuration, and with the balloon 30 being selectively inflated or deflated with an inflating mechanism;
e. with the catheter head 13 and the catheter end cap 14 each being biased in a deflated configuration, with the catheter head 13 and the catheter end cap 14 each being selectively expandable or retractable in response to the inflation or deflation of the balloon 30; with the expanded catheter head 13 and the expanded catheter end cap 14 each anchoring an arterial wall at the target site to further provide the isolated environment for arterial plaque removal; with the catheter head 13 and the catheter end cap 14 each defining a corresponding plurality of openings therethrough for maintaining continuous blood flow during use of the catheter apparatus within the arterial wall; and with the catheter head 13 comprising a tubular array 16 extending therefrom, with the tubular array 16 comprising an inflow tube 5 for transporting a treatment solution to the target site, an outflow tube 6 for removing the treatment solution containing the plaque from the target site, and a guide tube 29 for receiving a guide-wire 27 therethrough for positioning the catheter apparatus 1 at the target site;
f. with the catheter body 15 being separated into a first layer 2, a second layer 8, and a third layer 10, and with the catheter end cap 14 further defining an opening at a distal end of the guide tube 29 for receiving the guide-wire 27 therethrough, wherein the plaque, the treatment solution, or the treatment solution containing the plaque do not enter into the second layer 8 or the third layer 8 of the catheter body 15 and do not enter the bloodstream;
g. with the first layer 2 of the catheter body 15 comprising a plurality of flap members 33 arranged and spaced apart along a length of the first layer 2 of the catheter body 15, with each of the plurality of flap members 33 defining at least one pore 7 therethrough, and with a distal portion of both the inflow tube 5 and the outflow tube 6 extending within the first layer 2 for the treatment solution to pass from the inflow tube 5 through the at least one pore 7 of each of the plurality of flap members 33 to the target site and to remove the treatment solution containing the plaque back out the at least one pore 7 of each of the plurality of flap members out the outflow tube 6 and away from the target site;
h. with the second layer 8 of the catheter body 15 comprising (i) an outer surface 18, (ii) an inner surface 19, (iii) a plurality of strut members 9, and (iv) defining a plurality of chamber gaps 20 among the plurality of strut members 9, with the each of the plurality of strut members 9 being spaced apart and affixed along a length between the inner surface 19 of the second layer 8 of the catheter body 15 and an outer surface 21 of the third layer 10 of the catheter body 15 to allow for continuous blood flow during the treatment procedure; and
i. with the third layer 10 of the catheter body 15 comprising a core sheath 26 defining a core 10 having the guide tube 29 therein for receiving the guide-wire 27 therethrough, with the core sheath 26 extending the length of the catheter body 15, with the core 10 further defining opposing open ends; and with the third layer 10 comprising the outer surface 21;
j. wherein the guide tube 29 of the tubular array of the catheter apparatus 1 is removably insertable over the guide-wire 27 as the catheter apparatus 1 is drawn to and positioned at the target site for the treatment procedure;
k. wherein the inflating mechanism is actuated to selectively inflate the balloon 30 which laterally expands and supplies tension to the catheter head 13 and the catheter end cap 14 to outwardly flare, expand, and inflate both the catheter head 13 and the catheter end cap 14 thereby removably anchoring the catheter apparatus 1 to the arterial wall to provide structural support, and isolating the target site for arterial plaque removal within the first layer 2 of the catheter body 15 using the treatment procedure for providing an inflow of the treatment solution through the inflow tube 5 and for removing the treatment solution containing the plaque out the outflow tube 6 while simultaneously maintaining continuous blood flow through the plurality of openings defined in the catheter head 13, the catheter end cap 14, and through the second layer 8 of the catheter body 15; wherein the treatment procedure is selectively repeated to remove the arterial plaque, or the catheter apparatus 1 is selectively adjusted about the target site or the arterial wall before repeating the treatment procedure to remove the arterial plaque; and wherein after completion of the treatment procedure, the balloon 30 is selectively deflated with the tension upon the balloon 30 being removed from the catheter head 13 and the catheter end cap 14 to return each to the biased, deflated configuration, before slidably withdrawing the catheter apparatus 1 along the guide-wire 27 from the target site. The core sheath 26 may be selectively expandable or retractable in response to the balloon 30 being selectively inflated or deflated during the treatment procedure. The balloon 30 may circumscribe the core sheath 26 within the catheter body 15.

In another preferred embodiment, the invention is a catheter apparatus 1 for arterial plaque removal in an isolated environment while maintaining continuous blood flow in a bloodstream during a treatment procedure, with the catheter apparatus 1 being positioned at a target site during the treatment procedure, the catheter apparatus comprising:
- a. a catheter head 13 at a proximal end 13 of the catheter apparatus 1;
- b. a catheter body 15;
- c. a catheter end cap 14 at a distal end 14 of the catheter apparatus 1; and
- d. a balloon 30 within the catheter body 15, with the balloon 30 being biased in a deflated configuration, and with the balloon 30 being selectively inflated or deflated with an inflating mechanism;
- e. with the catheter head 13 and the catheter end cap 14 each being biased in a deflated configuration, with the catheter head 13 and the catheter end cap 14 each being selectively expandable or retractable in response to the inflation or deflation of the balloon 30; with the expanded catheter head 13 and the expanded catheter end cap 14 each anchoring an arterial wall at the target site to further provide the isolated environment for arterial plaque removal; with the catheter head 13 and the catheter end cap 14 each defining a corresponding plurality of openings therethrough for maintaining continuous blood flow during use of the catheter apparatus 1 within the arterial wall; and with the catheter head 13 comprising a tubular array 16 extending therefrom, and with the tubular array 16 comprising an inflow tube 5 for transporting a treatment solution to the target site, and an outflow tube 6 for removing the treatment solution containing the plaque from the target site;
- f. with the catheter body 15 being separated into an outer shell 2, a chamber 8, and a core sheath 26, wherein the plaque, the treatment solution, or the treatment solution containing the plaque do not enter into the chamber 8 or the core sheath 26 and do not enter the bloodstream;
- g. with the outer shell 2 of the catheter body 15 comprising a plurality of flap members 33 spaced apart along the outer shell, with each of the plurality of flap members 33 defining at least one pore 7 therethrough, and with a distal portion of both the inflow tube 5 and the outflow tube 6 extending within the outer shell 2 for the treatment solution to pass from the inflow tube 5 through the at least one pore 7 of each of the plurality of flap members 33 to the target site and to remove the treatment solution containing the plaque back out the at least one pore 7 of each of the plurality of flap members 33 out the outflow tube 6 and away from the target site;
- h. with the chamber 8 of the catheter body 15 comprising (i) an outer surface 18, (ii) an inner surface 19, (iii) a plurality of strut members 9, and (iv) defining a plurality of chamber gaps 20 among the plurality of strut members 9, with the each of the plurality of strut members 9 being spaced apart and affixed along a length between the inner surface 19 of the chamber 8 and an outer surface 21 of the core sheath 26 to allow for continuous blood flow in the bloodstream; and
- i. with the core sheath 26 of the catheter body 15 defining a core 10 that defines opposing open ends, and with the core sheath 26 comprising the outer surface 21;
- j. wherein the catheter apparatus 1 is slidably drawn to and positioned at the target site for the treatment procedure for arterial plaque removal, with the balloon 30, the catheter head 13, and the catheter end cap 14 are each biased in a deflated configuration; and
- k. wherein the inflating mechanism is actuated to selectively inflate the balloon 30 which laterally expands and supplies tension to the catheter head 13 and the catheter end cap 14 to outwardly flare, expand, and inflate both the catheter head 13 and the catheter end cap 14 thereby removably anchoring the catheter apparatus 1 to the arterial wall to provide structural support, and isolating the target site for arterial plaque removal within the outer shell 2 of the catheter body 15 using the treatment procedure for providing an inflow of the treatment solution through the inflow tube 5 and for removing the treatment solution containing the plaque out the outflow tube 6 while simultaneously maintaining continuous blood flow through the plurality of openings defined in the catheter head 13, the catheter end cap 14, and through the chamber 8 of the catheter body 15; wherein the treatment procedure is selectively repeated to remove the arterial plaque, or the catheter apparatus is selectively adjusted about the target site or the arterial wall before repeating the treatment procedure to remove the arterial plaque; and wherein after completion of the treatment procedure, the balloon 30 is selectively deflated with the tension upon the balloon 30 being removed from the catheter head 13 and the catheter end cap 14 to return each to the biased, deflated configuration before slidably withdrawing the catheter apparatus 1 from the target site.

In yet another embodiment, the catheter apparatus (or catheter device) 1 comprises (includes or has):

a) a first layer being an outer sleeve 2, a second layer defining a chamber 8, and a third layer defining a core 10;

b) the outer sleeve 2 comprising a proximal end 13 of a catheter head, a longitudinal sleeve body, and a distal end 14 of a catheter end cap, with the proximal end 13 of the outer sleeve 2 further having two sleeve tubes 5, 6 each extending outwardly from the proximal end 13 of the outer sleeve 2 to form part of a tubular array 16, with the sleeve body further defining a plurality of pores 7 therethrough;

c) a chamber 8 defining a hollow interior 17, and comprising an outer surface 18, an inner surface 19, and a plurality of spaced apart strut members 9 each of which is affixed to the chamber inner surface 19 and the core outer surface 21, with a chamber gap 20 defined between an inner surface 22 of the outer sleeve 2 and the outer surface 18 of the chamber 8; and d) a core 10 comprising a proximal end 23, a distal end 24, an end cap 25 defining an open ended hollow sheath 26 for removably receiving a guide-wire 27, a core body 28, a core tube 29, an outer surface 21, and a selectively inflatable balloon 30.

The outer sleeve 2 is essentially the catheter's 1 first layer or exterior of the catheter. The outer sleeve 2 is essentially a sleeve or shell that surrounds the chamber 8 and the core 10 of the catheter apparatus 1. The outer sleeve 2 has a proximal end 13 (or proximal portion) of the catheter head 13, a distal end 14 (or distal portion) of the catheter end cap 14, and a longitudinal sleeve body 15. When deflated, the catheter head, the catheter end cap, and the outer sleeve essentially form a longitudinal member that extends the length of the catheter apparatus. In one embodiment, the catheter member is preferably a cylindrical shape when in a deflated configuration.

Two options are available when inflating the balloon during plaque removal. In one embodiment (shown in the figures), the entire device head and the end cap of the catheter, along with the respective proximal portion and distal portion of the outer sleeve, selectively inflate or flare outwardly into an hourglass shape, in relation to the catheter body, using various tension within the selectively inflatable balloon core. The tension of the inflating balloon decreases starting in the middle of the apparatus and moves towards the proximal end and the distal end of the catheter apparatus. The inflated balloon results in a corresponding expanded, hourglass-shaped proximal portion and distal portion of the outer sleeve of the catheter body, along with the catheter head and catheter end cap. In another embodiment, the proximal end and the distal end of the balloon, and consequently the catheter head and catheter end cap, inflate to create an isolated middle area of the catheter body to form an hourglass shape. When deflated, the outer sleeve with the catheter head and the catheter end cap are preferably the length of the catheter body, and have a diameter of approximately 6 mm (with the size subject to change depending on situation), and thickness of approximately 2× the catheter core thickness. Other proportional sizing are contemplated. The outer sleeve is preferably made from a highly elastic material. The opposing ends of the outer sleeve and the catheter head, the chamber, and the core and the catheter end cap are substantially flush, and are preferably at the same height.

As shown in FIGS. 1-2, 4, 10-11, 13, 19-22, the proximal end 13 of the outer sleeve 2, or the catheter head, has a tubular array. The tubular array has at least two sleeve tubes 5, 6, which are essentially the inflow tube and the outflow tube. A third sleeve tube or guide tube member receives a conventional guide-wire 27 therethrough. The two sleeve tubes 5, 6 are a first sleeve tube 5 and a second sleeve tube 6, with a proximal portion of each sleeve tube extruding outwardly from the outer sleeve 2 and a distal portion of each sleeve tube 5, 6 defined within the sleeve body 15 of the outer sleeve 2 or within the first layer catheter body through the catheter head. The proximal end and the distal end of each sleeve tube is open ended. The sleeve tubes do not extend the entire length of the outer sleeve or the catheter body and do not extend out the distal end of the outer sleeve, or alternatively, out the catheter end cap. The two sleeve tubes 5, 6 are essentially parallel to each other, and are separated by the chamber 8 and the core 10 therebetween. In this embodiment, the two sleeve tubes 5, 6 are part of the structure of the outer sleeve 2 or the catheter head 13 with which it connects and are not removable.

As shown in the figures, the proximal portions of each sleeve tube extend from the proximal end of the outer sleeve, then tapers at an inward angle toward the opposite sleeve tube, then substantially straightens to parallel with the outer sleeve to abut the core tube 29 (or guide tube 29) to essentially form a Y-shaped or inverted fork-shaped tubular array 16 or tubular cluster. During inflation, the sleeve tubes allow for some flexibility and spread slightly further apart from the core tube for minimal movement. Although substantially physically stationary, each of the first sleeve tube and the second sleeve tube is interchangeable for functional use as an inflow tube or an outflow tube for the treatment solution. References in this disclosure of the inflow tube as the first sleeve tube and the outflow tube as the second sleeve tube are provided for simplicity purposes only. During the procedure, the sleeve tubes are used for treatment solution in and solution out to at the target site. The dimensions of the first sleeve tube and the second sleeve tube are essentially identical and are sized to accommodate as an adequate an inflow tube and an outflow tube.

In another embodiment, the catheter head 13 or the proximal end portion 13 of the outer sleeve 2 further defines a first open-ended bore 3 therein and a second open-ended bore 4 therein, with the first sleeve tube 5 and the second sleeve tube 6 extending from the first bore 3 and the second bore 4, respectively. The first bore and the second bore do not extend out through the opposing distal end of the outer sleeve. The first bore and the second bore are essentially parallel to each other, but are separated by the chamber and the core. The first bore and the second bore are essentially sleeve tube holders for the respective first sleeve tube and second sleeve tube. The first bore and the second bore are sized to tightly fit or encase the respective first sleeve tube and second sleeve tube.

The distal end 14 of the outer sleeve 2 may further include a rim 31 circumscribing and flush with the distal ends of the chamber 32 and the core 24. The distal end 14 of the outer sleeve 2 does not have any bores or sleeve tubes extending therefrom. In one embodiment shown in FIGS. 2, 6, 11, and 15, the outer sleeve 2 distal end 14 or end cap 14 formed a contoured edge, a beveled edge, or a fillet edge for insertion ease as the device head is inserted through the artery and guided toward the affected area.

The first layer of the catheter body or the sleeve body 15 of the outer sleeve 2 is a longitudinal, stretchable member. The sleeve body 15 defines a plurality of flap members 33 spaced apart along the sleeve body, each of which defines at least one pores 7 therein. Each pore 7 is essentially a pressure regulated air pore. Each pore is preferably reinforced. Each pore preferably has a maximum, effective size for treatment solution control, while minimizing the blood leakage rate. In one embodiment, the plurality of flap members 33 with pores 7 are preferably spaced along the length and width of the sleeve body 15 in a uniform pattern. In another embodiment, a specific pattern is not required as long as each of the plurality of pores are spaced apart from each other. Each pore 7 has a slightly movable flap member 33 to accommodate solution flow from the sleeve tubes 5, 6. In a preferred embodiment, each flap member 33 of a pore has a small gap or slit for the solution flow. The flap member gap preferably has a cross-hair configuration. The cross-hair gap 33 is large enough for solution flow but small enough to prevent excessive transverse blood flow passage or blood flow leakage. The structure of the pores is important to this device because a force must be applied so that a liquid can pass through the pores in either direction. The pores allow the dissolvent and the resulting solution to pass through inflow tube and outflow tube using a vacuum force, but do not grant blood passage because the pressure is not strong enough for blood to pass through the pores.

The second layer of the catheter 1 is a chamber 8. As shown in the FIG. 1-2, 7-9, the chamber 8 is a longitudinal hollow chamber located between the outer sleeve 2 or first layer of the catheter body 2 and the core 10 or third layer of the catheter body 10. A chamber gap 20 is located between an inner surface (membrane) 22 of the outer sleeve 2 and an outer surface (membrane) 19 of the chamber 8. The chamber 8 defines essentially an open ended proximal end 34 and an open ended distal end 35. The chamber 8 has a plurality of strut members 9 that are spaced along the length and width of the chamber to create hollow spaces for the blood to move through during the procedure.

Each strut member 9 is essentially a thin plate or membrane having one lateral end affixed to an inner surface (membrane) of the chamber 8, an opposing lateral end affixed to an outer surface (membrane) 21 of the core 10, with a top and a bottom of the strut member being unobstructed. The configuration and layout of the collective plurality of strut members allow for unobstructed continuous blood flow along the length of the device during treatment, even when the device is inflated. Each individual strut member 9 does not extend the entire length of the device 1.

Each strut member is made from a flexible, elastic material that is firmer than the elastic material used for the outer sleeve and for the core. The strut members 9 are not in contact with the same surface as the outer sleeve plurality of flap members 7 having at least one pore for use with a treatment solution. Each strut member is preferably a rectangular stilt that is sized and spaced to allow appropriate stretch during device inflation. The strut members not only aid in continuous blood flow, but also are carefully positioned to avoid obstructing the core functionality of the pores.

The third layer of the catheter 1 is the core 10. The core 10 is the innermost layer of the catheter 1. The core 10 has a proximal end 23, a distal end 24 having an end cap 25 defining an open ended hollow sheath 26 extending therethrough, a longitudinal core body 28, a core tube 29 or guide tube extending from the proximal end 23 of the core 10. The core is essentially an open ended longitudinal tubular member. The plurality of strut members 9 from the chamber are each affixed to the outer surface 21 of the core 10. A selectively inflatable balloon 30 circumscribes the sheath 26.

The core tube 29 or guide tube 29 extends from proximal end 23 of the core 10 to meet and abut between the two sleeve tubes 5, 6. The core tube 29 is open ended, and holds the guide-wire 27, which is insertable therethrough. A core sheath 26 extends within the length of the core body 28 from the proximal end 23 of the core 10 to the distal end 24 of the core 10. The balloon 30 is located outside the core sheath 26. The end cap 25 at the distal end 24 of the core 10 defines an opening smaller than the opening in the core tube 29. The end cap 25 is reinforced to support the hollow sheath 26 and the guide-wire 27 inserted therethrough. The guide-wire is insertable through the proximal end of the core tube through the core sheath and out the opening in the end cap. The core has a thickness that is preferably half the thickness of the sleeve. The core has a thickness that is preferably twice the thickness of each strut member. The core is made from the same elastic material as the outer sleeve. The three layers of the catheter device are independent, yet are affixed to each other.

The balloon structure and material are tighter substantially at or near the middle of the core and is more elastic and expandable toward the proximal end and the distal end of the balloon. The balloon 30 essentially extends the length of the interior of the core 10. Once inflated, this balloon configuration creates an isolated environment by abutting both the catheter head and the catheter end cap against the arterial wall. Inflating the balloon 30 essentially bends or inflates the proximal end portion and distal end portion of the outer sleeve 2, the catheter head, and the catheter end cap. The balloon is selectively inflated by an external, regulated air pump.

To use the invention for plaque removal within an artery, a conventional incision is made at the patient's groin or wrist, a conventional catheter is run through the artery with live imaging or real time imaging, for example with x-ray imaging, to show the targeted location. Dye may be injected to track blood flow and to confirm the blockage location. A small gauge guide-wire is inserted through the catheter. The original catheter is removed and replaced with the improved catheter device by inserting the core sheath over the guide-wire.

As shown in FIGS. 19-26, the improved catheter apparatus 1 is guided and positioned at the target area. The deflated outer sleeve 2 slidably travels along the artery, with the core sheath 26 insertable enclosing and traveling along the guide-wire 27 to the affected area or target site. The hourglass inflation of the outer sleeve 2 or catheter head and catheter end cap acts as a temporary, removable stent to support the artery wall during the procedure. The balloon 30 is inflated with the inflating mechanism. The solution containing membrane is essentially all one compartment within the outer sleeve or first layer of the catheter body. The plaque dissolving solution is outputted through the plurality of flap member pores via the inflow tube, and then vacuumed through the same pores via the outflow tube. This process repeats over and over again on an adjustable step-function. Solution output to problem-site occurs over a temporal step-function. Solution is constantly and continuously being either outputted through the pores, or inputted through the pores via an external vacuum force. The balloon 30 and the outer sleeve 2 expand or flare outwardly toward the arterial wall to create an isolated treatment area and to support the arterial wall without damaging the arterial wall. The plaque treatment solution travels through the inflow tube and exits through outflow tube and the flap members having pores, and are each within the same space inside the outer sleeve 2 yet remain isolated from the continuous blood flow travelling through the chamber 8 around the plurality of strut members 9 and out the distal end 35 of the chamber 8 and end cap. The plaque waste is removed and vacuumed using the outflow tube. Due to the separate, distinct layers of the catheter apparatus, plaque waste or other treatment solution within the outer sleeve does not enter the bloodstream flowing through the chamber. After treatment, the catheter apparatus is deflated and moved either to other site(s) or removed from the patient's body.

This catheter apparatus is not limited to use only with peripheral arteries. Instead, it may be used with many arteries (size permitting) because of the design's gentle nature and modality. Because the entire catheter apparatus is removed after the procedure, the risk of infection due to a foreign body (such as a stent) remaining in the body is eliminated.

In one embodiment shown in FIGS. 19-26, a method of using a catheter apparatus during a treatment procedure for arterial plaque removal in an isolated environment while maintaining continuous blood flow, with the catheter apparatus being insertable over a guide-wire and positioned at a target site during the treatment procedure, the method comprising the steps of:

1. slidably inserting the guide-wire through the catheter apparatus and slidably traveling and drawing the catheter apparatus to the target site within the arterial wall, with the catheter apparatus being biased in a deflated configuration;

2. the balloon of the catheter apparatus of claim 1 being selectively inflated using the inflating mechanism, with tension from the inflating mechanism being applied to the proximal portion and the distal portion of the balloon resulting in expansion of both the catheter head and the catheter end cap to flare outwardly about the catheter body, and with the actuated, inflated catheter head and the catheter end cap creating an isolated environment at the target site from the bloodstream during the treatment procedure and further anchoring the apparatus within the arterial wall, with the second layer of the catheter apparatus maintaining continuous blood flow within the arterial wall;

3. selectively actuating the inflow tube and pushing a treatment solution through the inflow tube and into the first layer of the catheter body, with the treatment solution comprising a plaque dissolving solvent being further pushed through the at least one pore of each of the plurality of flap members of the first layer of the catheter body to impact the plaque at the target site;

4. upon treatment of the plaque at the target site, selectively disengaging the inflow tube and selectively actuating the outflow tube to apply outflow pressure, thereby outputting and vacuuming the treated plaque and waste from the treatment solution away from the target site over a temporal step-function, back through the at least one pore of each of the plurality of flap members, and into the outflow tube for disposal; and 5. after treatment at the target site, wherein disengaging the inflating mechanism to deflate the balloon, returning the proximal portion and the distal portion of the balloon to a biased, deflated configuration; wherein as the tension from the inflated balloon to the catheter head and the catheter end cap dissipates, both the catheter head and the catheter end cap retract to the biased deflated configuration, and wherein withdrawing the catheter apparatus along the guide-wire from the target site. The inflating mechanism further comprising an external, air pressure regulated inflating mechanism.

FIGS. 7 and 8 depict cross-sectional views of the catheter apparatus shown in an inflated configuration, with the catheter head and the catheter end cap each being inflated. Here, the balloon has already been deflated. These figures reflect the mid-deflation process as tension against the catheter head and the catheter end cap is removed.

Figure 23:
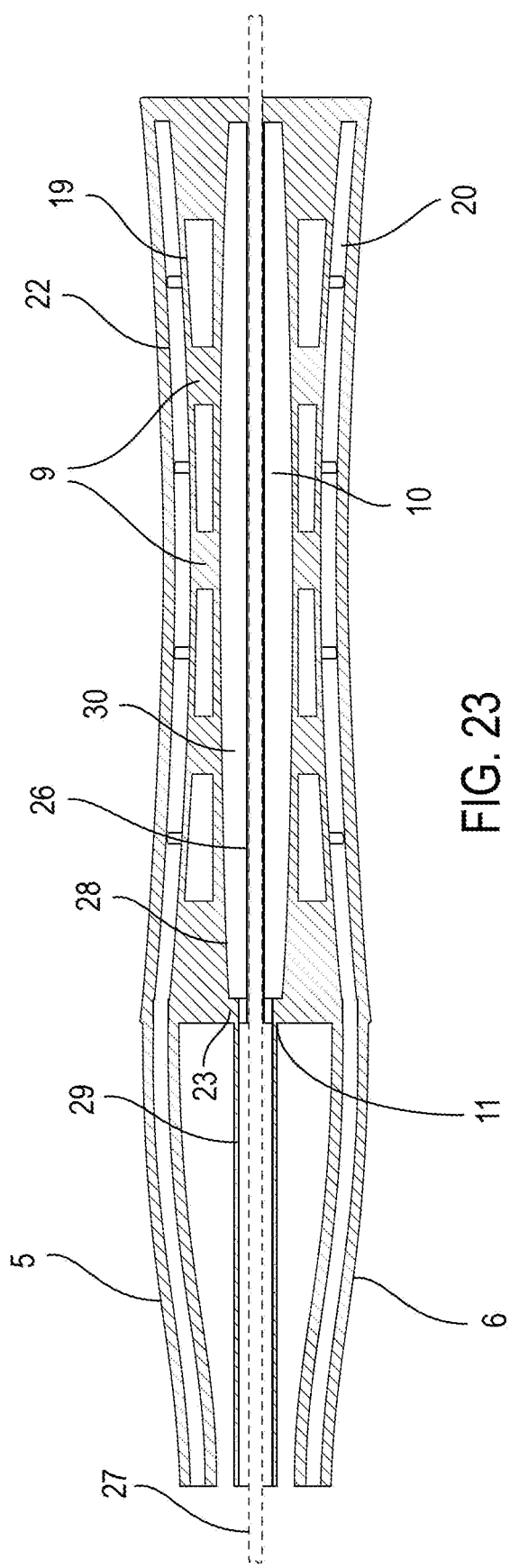
FIG. 23 is a lateral cross-section view of FIG. 3, showing the balloon, the catheter head, and the end cap each being inflated.
Figure 24:
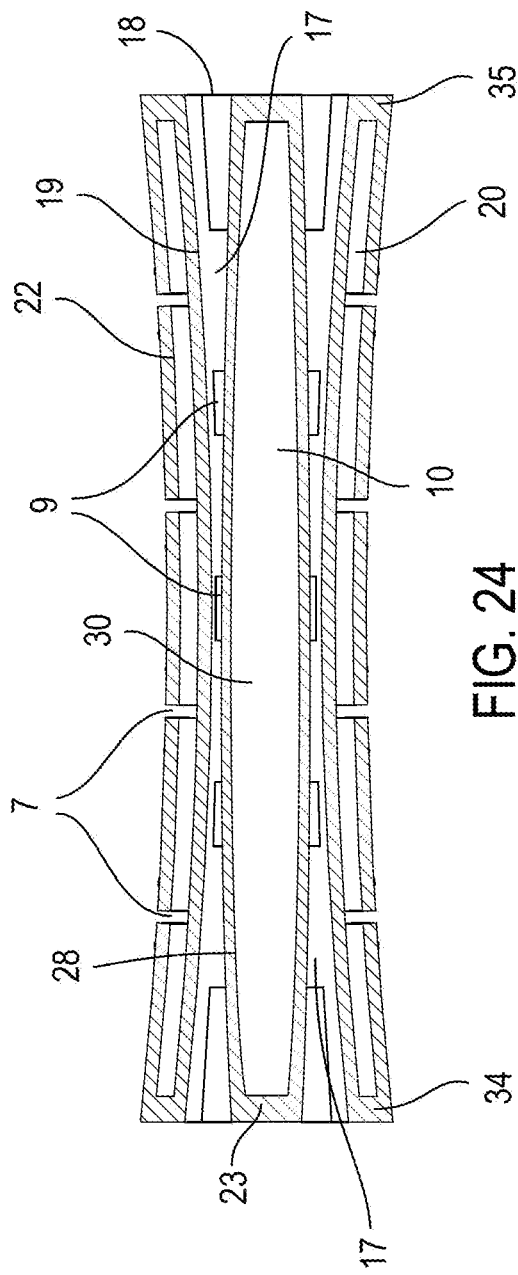
FIG. 24 is another lateral cross-section view of FIG. 3, showing the balloon, the catheter head, and the end cap each being inflated.

FIGS. 23 and 24 depict cross-sectional views of the catheter apparatus shown in an inflated configuration, with the catheter head, the catheter end cap, and the balloon each being inflated. Here, the tension applied to the proximal portion and the distal portion of the balloon impacts the proximal portion and the distal portion of the catheter apparatus, namely, the catheter head and the catheter end cap to also expand, inflate, or flare outwardly. The middle portion of the catheter body minimally expands, with this hour-glass shape aiding in the isolated environment during treatment.

Figure 25:
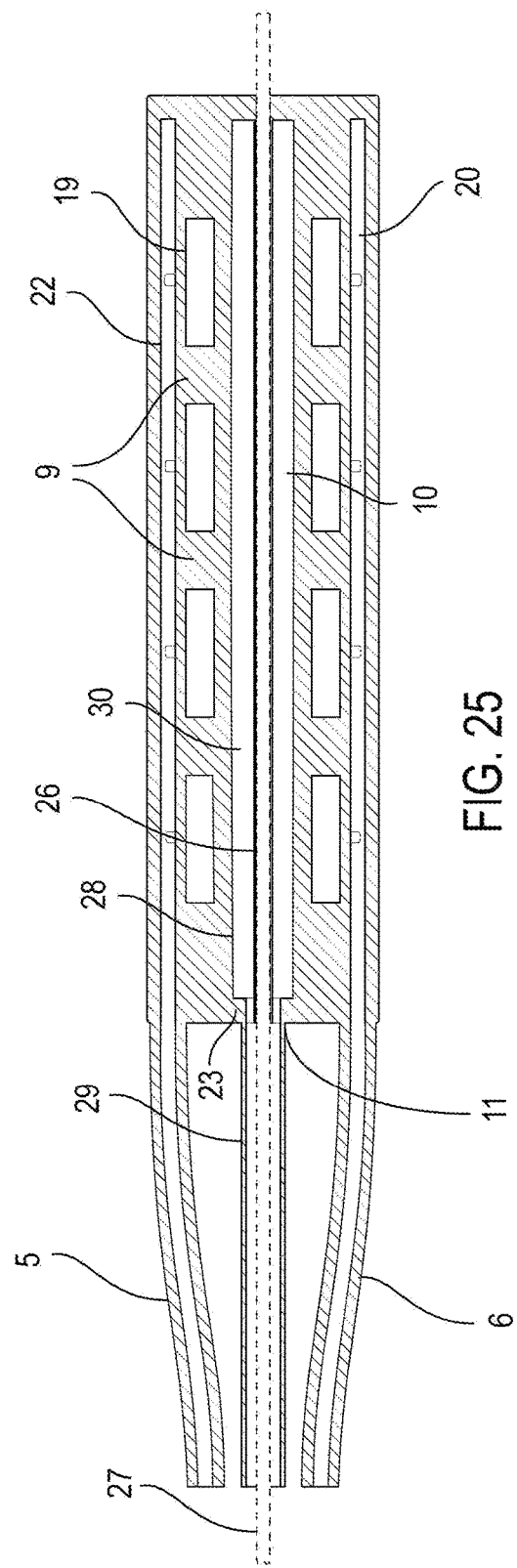
FIG. 25 is a lateral cross-section view of FIG. 12, showing the balloon, the catheter head, and the end cap each being deflated.
Figure 26:
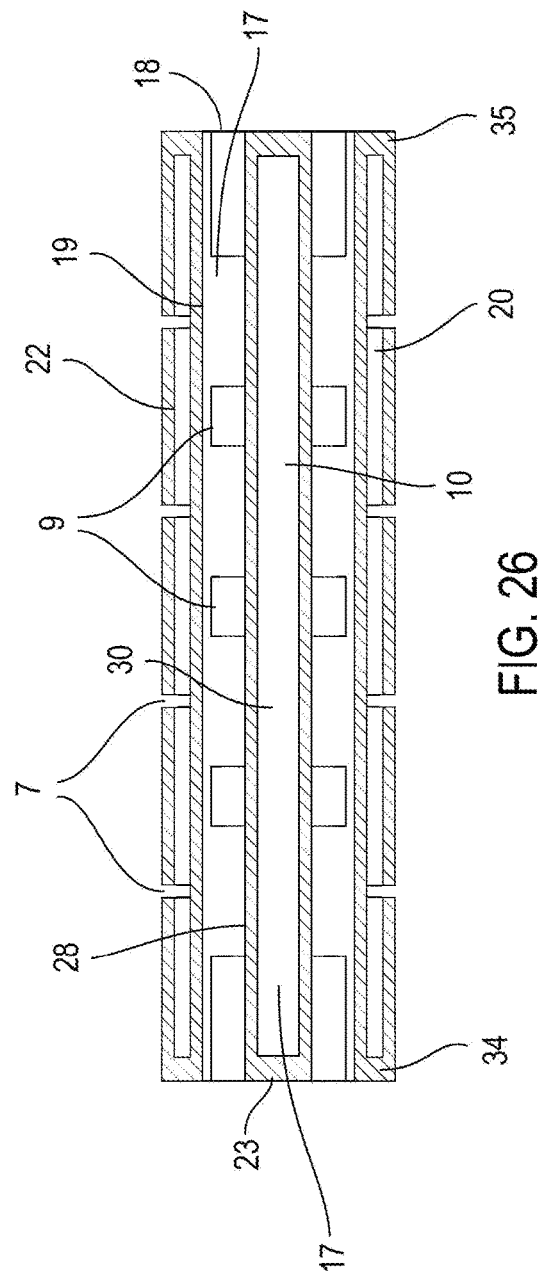
FIG. 26 is another lateral cross-section view of FIG. 12, showing the balloon, the catheter head, and the end cap each being deflated.

FIGS. 25 and 26 depict cross-sectional views of the catheter apparatus shown in a deflated configuration, with the catheter head and the catheter end cap each being deflated. Here, the balloon has been inflated but has not yet applied enough tension to the catheter head and the catheter end cap. These figures reflect the mid-inflation process as tension is being applied to the catheter head and the catheter end cap.

Those skilled in the art who have the benefit of this disclosure will appreciate that it may be used as the creative basis for designing devices or methods similar to those disclosed herein, or to design improvements to the invention disclosed herein; such new or improved creations should be recognized as dependent upon the invention disclosed herein, to the extent of such reliance upon this disclosure.

I claim:

1. A catheter apparatus for arterial plaque removal in an isolated environment while maintaining continuous blood flow in a bloodstream during a treatment procedure, with the catheter apparatus being insertable over a guide-wire and positioned at a target site during the treatment procedure, the catheter apparatus comprising:

a. a catheter head at a proximal end of the catheter apparatus;
b. a catheter body;
c. a catheter end cap at a distal end of the catheter apparatus; and
d. a balloon within the catheter body, the balloon being biased in a deflated configuration, and with the balloon being selectively inflated or deflated with an inflating mechanism;

e. the catheter head and the catheter end cap each being biased in a deflated configuration, the catheter head and the catheter end cap each being selectively expandable or retractable in response to the inflation or deflation of the balloon; wherein when the catheter head and the catheter end cap are expanded, the catheter head and the catheter end cap are configured to each anchor an arterial wall at the target site to further provide the isolated environment for arterial plaque removal; the catheter head and the catheter end cap each defining a corresponding plurality of openings therethrough for maintaining continuous blood flow during use of the catheter apparatus within the arterial wall; and the catheter head comprising a tubular array extending therefrom, the tubular array comprising an inflow tube for transporting a treatment solution to the target site, an outflow tube for removing the treatment solution containing the plaque from the target site, and a guide tube for receiving the guide-wire therethrough for positioning the catheter apparatus at the target site;

f. the catheter body being separated into a first layer, a second layer, and a third layer, and the catheter end cap further defining an opening at a distal end of the guide tube for receiving the guide-wire therethrough, wherein the plaque, the treatment solution, or the treatment solution containing the plaque do not enter into the second layer or the third layer of the catheter body and do not enter the bloodstream;

g. the first layer of the catheter body comprising a plurality of flap members arranged and spaced apart along a length of the first layer of the catheter body, each of the plurality of flap members defining at least one pore therethrough, and a distal portion of both the inflow tube and the outflow tube extending within the first layer for the treatment solution to pass from the inflow tube through the at least one pore of each of the plurality of flap members to the target site and to remove the treatment solution containing the plaque back out the at least one pore of each of the plurality of flap members out the outflow tube and away from the target site;

h. the second layer of the catheter body comprising (i) an outer surface, (ii) an inner surface, (iii) a plurality of strut members defining a plurality of chamber gaps among the plurality of strut members, each of the plurality of strut members being spaced apart and affixed along a length between the inner surface of the second layer of the catheter body and an outer surface of the third layer of the catheter body to allow for continuous blood flow during the treatment procedure; and i. the third layer of the catheter body comprising a core sheath defining a core having the guide tube therein for receiving the guide-wire therethrough, with the core sheath extending a length of the catheter body, with the core further defining opposing open ends; and with the third layer comprising the outer surface;

j. wherein the guide tube of the tubular array of the catheter apparatus is removably insertable over the guide-wire as the catheter apparatus is drawn to and positioned at the target site for the treatment procedure;

k. wherein the inflating mechanism is configured to be actuated to selectively inflate the balloon which laterally expands and supplies tension to the catheter head and the catheter end cap to outwardly flare, expand, and inflate both the catheter head and the catheter end cap thereby removably anchoring the catheter apparatus to the arterial wall to provide structural support, and wherein the catheter apparatus is configured to isolate the target site for arterial plaque removal within the first layer of the catheter body using the treatment procedure for providing an inflow of the treatment solution through the inflow tube and for removing the treatment solution containing the plaque out the outflow tube while simultaneously maintaining continuous blood flow through the plurality of openings defined in the catheter head, the catheter end cap, and through the second layer of the catheter body; wherein the treatment procedure can be selectively repeated to remove the arterial plaque, or the catheter apparatus can be selectively adjusted about the target site or the arterial wall before repeating the treatment procedure to remove the arterial plaque; and wherein after completion of the treatment procedure, the balloon can be selectively deflated with the tension upon the balloon being removed from the catheter head and the catheter end cap to return each of the catheter head and catheter end cap to the biased, deflated configuration, before slidably withdrawing the catheter apparatus along the guide-wire from the target site.

2. The catheter apparatus of claim 1, a proximal portion of both the inflow tube and the outflow tube of the tubular array are each open-ended and each extend from the catheter head, then both tapering inwardly toward each other before straightening and being configured parallel to the guide tube.

3. The catheter apparatus of claim 2, the inflow tube and the outflow tube of the tubular array each further comprising a distal portion that extends within the first layer of the catheter body and positioned in proximity to the plurality of flap members each of which defines the at least one pore for the treatment solution to travel from the inflow tube through each of the at least one pore to the target site then back through the at least one pore and withdrawn through the outflow tube.

4. The catheter apparatus of claim 1, the at least one pore of each of the plurality of flap members defining reinforced, pressure regulated air pores for treatment solution control while minimizing transverse blood flow leakage during the treatment procedure, wherein each of the plurality of flap members are spaced apart along the length and a width of the catheter body, and wherein each of the plurality of flap members accommodate movement for treatment solution flow to and from the tubular array.

5. The catheter apparatus of claim 1, the second layer of the catheter body comprising a longitudinal hollow chamber located between the first layer of the catheter body and the third layer of the catheter body.

6. The catheter apparatus of claim 5, each of the plurality of strut members of the catheter body being segmented and comprising a first lateral end affixed to an inner surface of the chamber of the catheter body, an opposing second lateral end affixed to an outer surface of the third layer of the catheter body, and a top and a bottom being unobstructed and unaffixed, wherein the plurality of strut members are not in contact with a same surface as the plurality of flap members of the first layer of the catheter body.

7. A method of using the catheter apparatus of claim 1 during the treatment procedure for arterial plaque removal in the isolated environment while maintaining continuous blood flow, the catheter apparatus being insertable over the guide-wire and positioned at the target site during the treatment procedure, the method comprising the steps of:
 a. slidably inserting the guide-wire through the catheter apparatus and slidably traveling and drawing the catheter apparatus to the target site within the arterial wall, the catheter apparatus being biased in a deflated configuration;
 b. the balloon of the catheter apparatus being selectively inflated using the inflating mechanism, with tension from the inflating mechanism being applied to the proximal portion and the distal portion of the balloon resulting in expansion of both the catheter head and the catheter end cap to flare outwardly about the catheter body, and with the actuated, inflated catheter head and the catheter end cap creating an isolated environment at the target site from the bloodstream during the treatment procedure and further anchoring the apparatus within the arterial wall, with the second layer of the catheter apparatus maintaining continuous blood flow within the arterial wall;
 c. selectively actuating the inflow tube and pushing the treatment solution through the inflow tube and into the first layer of the catheter body, with the treatment solution comprising a plaque dissolving solvent being further pushed through the at least one pore of each of the plurality of flap members of the first layer of the catheter body to impact the plaque at the target site;
 d. upon treatment of the plaque at the target site, selectively disengaging the inflow tube and selectively actuating the outflow tube to apply outflow pressure, thereby outputting and vacuuming the treated plaque and waste from the treatment solution away from the target site over a temporal step-function, back through the at least one pore of each of the plurality of flap members, and into the outflow tube for disposal; and
 e. after treatment at the target site, wherein disengaging the inflating mechanism to deflate the balloon, returning the proximal portion and the distal portion of the balloon to the biased, deflated configuration; wherein as the tension from the inflated balloon to the catheter head and the catheter end cap dissipates, both the catheter head and the catheter end cap retract to the biased deflated configuration, and wherein withdrawing the catheter apparatus along the guide-wire from the target site.

8. The method of claim 7, wherein the inflating mechanism further comprising an external, air pressure regulated inflating mechanism.

9. A catheter apparatus for arterial plaque removal in an isolated environment while maintaining continuous blood flow in a bloodstream during a treatment procedure, the catheter apparatus configured to be positioned at a target site during the treatment procedure, the catheter apparatus comprising:
 a. a catheter head at a proximal end of the catheter apparatus;
 b. a catheter body;
 c. a catheter end cap at a distal end of the catheter apparatus; and
 d. a balloon within the catheter body, with the balloon being biased in a deflated configuration, and with the balloon being selectively inflated or deflated with an inflating mechanism;
 e. the catheter head and the catheter end cap each being biased in a deflated configuration, the catheter head and the catheter end cap each being selectively expandable or retractable in response to the inflation or deflation of the balloon; wherein when the catheter head and the catheter end cap are expanded, the catheter head and the catheter end cap are configured to each anchor an arterial wall at the target site to further provide the isolated environment for arterial plaque removal; the catheter head and the catheter end cap each defining a corresponding plurality of openings therethrough for maintaining continuous blood flow during use of the catheter apparatus within the arterial wall; and the catheter head comprising a tubular array extending therefrom, and the tubular array comprising an inflow tube for transporting a treatment solution to the target site, and an outflow tube for removing the treatment solution containing the plaque from the target site;

f. the catheter body being separated into an outer shell, a chamber, and a core sheath, wherein the plaque, the treatment solution, or the treatment solution containing the plaque do not enter into the chamber or the core sheath and do not enter the bloodstream;

g. the outer shell of the catheter body comprising a plurality of flap members spaced apart along the outer shell, with each of the plurality of flap members defining at least one pore therethrough, and with a distal portion of both the inflow tube and the outflow tube extending within the outer shell for the treatment solution to pass from the inflow tube through the at least one pore of each of the plurality of flap members to the target site and to remove the treatment solution containing the plaque back out the at least one pore of each of the plurality of flap members out the outflow tube and away from the target site;

h. the chamber of the catheter body comprising (i) an outer surface, (ii) an inner surface, (iii) a plurality of strut members defining a plurality of chamber gaps among the plurality of strut members, with the each of the plurality of strut members being spaced apart and affixed along a length between an inner surface of the chamber and an outer surface of the core sheath to allow for continuous blood flow in the bloodstream; and i. the core sheath of the catheter body defining a core that defines opposing open ends, and with the core sheath comprising the outer surface;

j. wherein the catheter apparatus is configured to be slidably drawn to and positioned at the target site for the treatment procedure for arterial plaque removal, the balloon, the catheter head, and the catheter end cap are each biased in a deflated configuration; and k. wherein the inflating mechanism is configured to be actuated to selectively inflate the balloon which laterally expands and supplies tension to the catheter head and the catheter end cap to outwardly flare, expand, and inflate both the catheter head and the catheter end cap thereby removably anchoring the catheter apparatus to the arterial wall to provide structural support, and wherein the catheter apparatus is configured to isolate the target site for arterial plaque removal within the outer shell of the catheter body using the treatment procedure for providing an inflow of the treatment solution through the inflow tube and for removing the treatment solution containing the plaque out the outflow tube while simultaneously maintaining continuous blood flow through the plurality of openings defined in the catheter head, the catheter end cap, and through the chamber of the catheter body; wherein the treatment procedure can be selectively repeated to remove the arterial plaque, or the catheter apparatus can be selectively adjusted about the target site or the arterial wall before repeating the treatment procedure to remove the arterial plaque; and wherein after completion of the treatment procedure, the balloon can be selectively deflated with the tension upon the balloon being removed from the catheter head and the catheter end cap to return each of the catheter head and the catheter end cap to the biased, deflated configuration before slidably withdrawing the catheter apparatus from the target site.

10. The catheter apparatus of claim 9, the catheter apparatus adapted to a substantially hour-glass shape when in the actuated, inflated configuration and being adapted to a substantially cylindrical shape when in the biased, deflated configuration.

11. The catheter apparatus of claim 9, a proximal portion of both the inflow tube and the outflow tube are each open-ended and extend from the catheter head, then both the inflow tube and the outflow tube taper inwardly toward each other before straightening and being configured parallel to each other.

12. The catheter apparatus of claim 11, the catheter head further comprising a guide tube for slidably receiving a guide-wire through the core of the core sheath of the catheter body and through the catheter end cap.

13. The catheter apparatus of claim 12, the tubular array comprising a plurality of sleeve tubes and the guide tube, with a first one of the plurality of sleeve tubes comprising the inflow tube and a second one of the plurality of the sleeve tubes comprising the outflow tube, with the use of the plurality of sleeve tubes being functionally interchangeable.

14. The catheter apparatus of claim 9, the at least one pore of each of the plurality of flap members being a reinforced, pressure regulated air pore for treatment solution control while minimizing transverse blood flow leakage during the treatment procedure, wherein each of the plurality of flap members are spaced apart along the length and a width of the outer sleeve of the catheter body, and wherein each of the plurality of flap members accommodate movement for the flow of the treatment solution from the inflow tube or the outflow tube.

15. The catheter apparatus of claim 14, each of the plurality of flap members of the at least one pore configured as a cross-hair gap.

16. The catheter apparatus of claim 9, each of the plurality of strut members being segmented and comprising a first lateral end affixed to the inner surface of the chamber, an opposing second lateral end affixed to an outer surface of the third layer of the catheter body, and a top and a bottom being unobstructed and unaffixed, wherein the plurality of strut members are not in contact with a same surface as the plurality of flap members of the outer shell of the catheter body.

* * * * *